US011045485B2

(12) United States Patent
Magnani et al.

(10) Patent No.: US 11,045,485 B2
(45) Date of Patent: Jun. 29, 2021

(54) GLYCOMIMETIC INHIBITORS OF PA-IL AND PA-IIL LECTINS

(71) Applicant: GlycoMimetics, Inc., Rockville, MD (US)

(72) Inventors: John L Magnani, Gaithersburg, MD (US); Arun K. Sarkar, North Potomac, MD (US)

(73) Assignee: GlycoMimetics, Inc., Rockville, MD (US)

( * ) Notice: Subject to any disclaimer, the term of this patent is extended or adjusted under 35 U.S.C. 154(b) by 0 days.

(21) Appl. No.: 16/069,685

(22) PCT Filed: Jan. 18, 2017

(86) PCT No.: PCT/US2017/013929
§ 371 (c)(1),
(2) Date: Jul. 12, 2018

(87) PCT Pub. No.: WO2017/127422
PCT Pub. Date: Jul. 27, 2017

(65) Prior Publication Data
US 2019/0060338 A1 Feb. 28, 2019

Related U.S. Application Data

(60) Provisional application No. 62/281,923, filed on Jan. 22, 2016.

(51) Int. Cl.
| | |
|---|---|
| *A61K 31/7034* | (2006.01) |
| *A61P 31/04* | (2006.01) |
| *A61P 11/00* | (2006.01) |
| *A61K 31/7036* | (2006.01) |
| *G01N 33/569* | (2006.01) |
| *A61K 47/55* | (2017.01) |

(52) U.S. Cl.
CPC ...... *A61K 31/7034* (2013.01); *A61K 31/7036* (2013.01); *A61K 47/552* (2017.08); *A61P 11/00* (2018.01); *A61P 31/04* (2018.01); *G01N 33/56911* (2013.01); *G01N 2333/21* (2013.01)

(58) Field of Classification Search
CPC . A61K 31/7034; A61K 31/7036; A61P 31/04; C07H 15/207
See application file for complete search history.

(56) References Cited

U.S. PATENT DOCUMENTS

| | | |
|---|---|---|
| 4,471,057 A | 9/1984 | Koprowski et al. |
| 4,851,511 A | 7/1989 | Hakomori et al. |
| 4,859,769 A | 8/1989 | Karlsson et al. |
| 4,876,199 A | 10/1989 | Hakamori |
| 4,925,796 A | 5/1990 | Bergh et al. |
| 4,946,830 A | 8/1990 | Pulverer et al. |
| 5,143,712 A | 9/1992 | Brandley et al. |
| 5,151,360 A | 9/1992 | Handa et al. |
| 5,211,937 A | 5/1993 | Brandley et al. |
| 5,268,364 A | 12/1993 | Kojima et al. |
| 5,304,640 A | 4/1994 | Lasky et al. |
| 5,352,670 A | 10/1994 | Venot et al. |
| 5,369,096 A | 11/1994 | Yamada et al. |
| 5,412,123 A | 5/1995 | Rao et al. |
| 5,444,050 A | 8/1995 | Kogan et al. |
| 5,464,778 A | 11/1995 | Cummings et al. |
| 5,464,815 A | 11/1995 | Chamow et al. |
| 5,470,843 A | 11/1995 | Stahl et al. |
| 5,484,891 A | 1/1996 | Lasky et al. |
| 5,486,536 A | 1/1996 | Ward et al. |
| 5,519,008 A | 5/1996 | Rao et al. |
| 5,527,785 A | 6/1996 | Bevilacqua et al. |
| 5,538,724 A | 7/1996 | Butcher et al. |
| 5,559,103 A | 9/1996 | Gaeta et al. |
| 5,576,305 A | 11/1996 | Ratcliffe |
| 5,580,858 A | 12/1996 | Ippolito et al. |
| 5,580,862 A | 12/1996 | Rosen et al. |
| 5,589,465 A | 12/1996 | Ishida et al. |
| 5,604,207 A | 2/1997 | DeFrees et al. |
| 5,618,785 A | 4/1997 | Heavner et al. |
| 5,622,937 A | 4/1997 | Kogan et al. |
| 5,639,734 A | 6/1997 | Esko et al. |
| 5,646,123 A | 7/1997 | Ippolito et al. |
| 5,646,248 A | 7/1997 | Sawada et al. |
| 5,648,344 A | 7/1997 | Brandley et al. |
| 5,654,282 A | 8/1997 | Tang et al. |
| 5,654,412 A | 8/1997 | Srivastava et al. |
| 5,658,880 A | 8/1997 | Dasgupta et al. |

(Continued)

FOREIGN PATENT DOCUMENTS

| | | |
|---|---|---|
| EP | 319253 A2 | 6/1989 |
| EP | 381310 A1 | 8/1990 |

(Continued)

OTHER PUBLICATIONS

Ernst, B. et al "From carbohydrate leads to glycomimetic drugs" Nat. Rev., vol. 8, pp. 661-677. (Year: 2009).*
Abraham, W.M. et al., "Selectin Blockade Prevents Antigen-induced Late Bronchial Response and Airway Hyperresponsiveness in Allergic Sheep," Am J. Respir Crit Care Med. 159: 1205-1214, 1999.
Acord, J. et al., "A rapid microplate method for quantifying inhibition of bacterial adhesion to eukaryotic cells," Journal of Microbiological Methods 60: 55-62, 2005.
Baeckstrom et al., "Purification and Characterization of a Membrane-bound and a Secreted Mucin-type Glycoprotein Carrying the Carcinoma-associated Sialyl-Le.sup.a Epitope on Distinct Core Proteins," J. Biol. Chem. 266(32):21537-21547, 1991.
Banteli, R. et al., "Potent E-Selectin Antagonists," Helvetica Chimica Acta 83(11): 2893-2907, 2000.
Belcher, J.D. et al., "Activated monocytes in sickle cell disease: potential role in the activation of vascular endothelium and vaso-occlusion," Blood 96(7):2451-2459, Oct. 1, 2000.

(Continued)

*Primary Examiner* — Leigh C Maier
(74) *Attorney, Agent, or Firm* — Finnegan, Henderson, Farabow, Garrett & Dunner, LLP

(57) ABSTRACT

Compounds, compositions, and methods for the diagnosis and/or treatment of medical conditions involving infections with and colonization by *Pseudomonas* bacteria including, for example, *Pseudomonas aeruginosa* in the lungs of patients with cystic fibrosis are described.

18 Claims, 15 Drawing Sheets

(56) References Cited

U.S. PATENT DOCUMENTS

| | | |
|---|---|---|
| 5,663,151 A | 9/1997 | Martel et al. |
| 5,679,321 A | 10/1997 | Dasgupta et al. |
| 5,679,644 A | 10/1997 | Rao et al. |
| 5,686,426 A | 11/1997 | Martel et al. |
| 5,693,621 A | 12/1997 | Toepfer et al. |
| 5,695,752 A | 12/1997 | Rosen et al. |
| 5,710,023 A | 1/1998 | Collins et al. |
| 5,710,123 A | 1/1998 | Heavner et al. |
| 5,723,583 A | 3/1998 | Seed et al. |
| 5,728,685 A | 3/1998 | Abbas et al. |
| 5,739,300 A | 4/1998 | Toepfer et al. |
| 5,747,463 A | 5/1998 | Marinier et al. |
| 5,750,508 A | 5/1998 | Dasgupta et al. |
| 5,753,617 A | 5/1998 | Heavner et al. |
| 5,753,631 A | 5/1998 | Paulson et al. |
| 5,763,413 A | 6/1998 | Numata et al. |
| 5,763,582 A | 6/1998 | Rao et al. |
| 5,789,385 A | 8/1998 | Anderson et al. |
| 5,789,573 A | 8/1998 | Baker et al. |
| 5,795,958 A | 8/1998 | Rao et al. |
| 5,811,404 A | 9/1998 | De Frees et al. |
| 5,811,405 A | 9/1998 | Toepfer et al. |
| 5,817,742 A | 10/1998 | Toepfer et al. |
| 5,827,817 A | 10/1998 | Larsen et al. |
| 5,827,837 A | 10/1998 | Bevilacqua et al. |
| 5,830,871 A | 11/1998 | Wong et al. |
| 5,837,689 A | 11/1998 | Anderson et al. |
| 5,837,690 A | 11/1998 | Rao et al. |
| 5,840,679 A | 11/1998 | Larsen et al. |
| 5,854,218 A | 12/1998 | DeFrees |
| 5,858,983 A | 1/1999 | Seed et al. |
| 5,858,994 A | 1/1999 | Kretzschmar et al. |
| 5,880,091 A | 3/1999 | Cummings et al. |
| 5,916,910 A | 6/1999 | Lai |
| 5,919,768 A | 7/1999 | Korgan et al. |
| 5,919,769 A | 7/1999 | Tsukida et al. |
| 5,962,422 A | 10/1999 | Nagy et al. |
| 5,976,540 A | 11/1999 | Rittershaus et al. |
| 5,977,080 A | 11/1999 | Rosen et al. |
| 5,985,852 A | 11/1999 | Nagy et al. |
| 5,994,402 A | 11/1999 | Rotstein et al. |
| 6,001,819 A | 12/1999 | Simon et al. |
| 6,001,988 A | 12/1999 | Parma et al. |
| 6,033,665 A | 3/2000 | Yednock et al. |
| 6,037,333 A | 3/2000 | Panjwani |
| 6,110,897 A | 8/2000 | Unverzagt et al. |
| 6,111,065 A | 8/2000 | Heavner et al. |
| 6,120,751 A | 9/2000 | Unger |
| 6,121,233 A | 9/2000 | Magnani et al. |
| 6,124,267 A | 9/2000 | McEver et al. |
| 6,133,239 A | 10/2000 | Handa et al. |
| 6,133,240 A | 10/2000 | Taylor et al. |
| 6,136,790 A | 10/2000 | Toepfer et al. |
| 6,169,077 B1 | 1/2001 | Oehrlein |
| 6,177,547 B1 | 1/2001 | Cummings et al. |
| 6,187,754 B1 | 2/2001 | Oehrlein |
| 6,193,973 B1 | 2/2001 | Tuttle |
| 6,193,979 B1 | 2/2001 | Rittershaus et al. |
| 6,197,752 B1 | 3/2001 | Schmidt et al. |
| 6,225,071 B1 | 5/2001 | Cummings et al. |
| 6,235,309 B1 | 5/2001 | Nagy et al. |
| 6,280,932 B1 | 8/2001 | Parma et al. |
| 6,309,639 B1 | 10/2001 | Cummings et al. |
| 6,387,884 B1 | 5/2002 | Magnani et al. |
| 6,391,857 B1 | 5/2002 | Magnani et al. |
| 6,407,135 B1 | 6/2002 | Lai et al. |
| 6,465,434 B1 | 10/2002 | Magnani et al. |
| 6,492,332 B1 | 10/2002 | Demopulos et al. |
| 6,503,885 B1 | 1/2003 | Kiso et al. |
| 6,515,117 B2 | 2/2003 | Ellsworth et al. |
| 6,528,487 B1 | 3/2003 | Heavner et al. |
| 6,569,998 B2 | 5/2003 | Cummings et al. |
| 6,683,056 B2 | 1/2004 | Washburn et al. |
| 6,844,125 B2 | 1/2005 | Bistrup et al. |
| 6,943,239 B2 | 9/2005 | Holgersson et al. |
| 6,967,093 B2 | 11/2005 | Bistrup et al. |
| 7,060,685 B2 | 6/2006 | Magnani et al. |
| 7,087,212 B2 | 8/2006 | Cantrell et al. |
| 7,300,656 B2 | 11/2007 | Ashkenazi et al. |
| 7,449,176 B2 | 11/2008 | Ashkenazi et al. |
| 7,517,980 B2 | 4/2009 | Magnani et al. |
| 7,563,760 B2 | 7/2009 | Larsen et al. |
| 8,258,290 B2 | 9/2012 | Magnani et al. |
| 2001/0046970 A1 | 11/2001 | Nagy et al. |
| 2001/0051370 A1 | 12/2001 | Bistrup et al. |
| 2002/0026033 A1 | 2/2002 | Cummings et al. |
| 2002/0028205 A1 | 3/2002 | Holgersson et al. |
| 2002/0031508 A1 | 3/2002 | Wagner et al. |
| 2002/0040008 A1 | 4/2002 | Wagner et al. |
| 2002/0132220 A1 | 9/2002 | Berens et al. |
| 2002/0164336 A1 | 11/2002 | Harrison et al. |
| 2002/0164748 A1 | 11/2002 | Bistrup et al. |
| 2002/0168366 A1 | 11/2002 | Stewart et al. |
| 2003/0012787 A1 | 1/2003 | Ashkenazi et al. |
| 2003/0012790 A1 | 1/2003 | Ashkenazi et al. |
| 2003/0018181 A1 | 1/2003 | Larsen et al. |
| 2003/0039683 A1 | 2/2003 | Cantrell et al. |
| 2009/0176717 A1 | 7/2009 | Magnani |
| 2011/0257380 A1* | 10/2011 | Ernst ............ C07H 15/207 536/17.9 |
| 2012/0329755 A1* | 12/2012 | Magnani ............ C07H 3/06 514/61 |

FOREIGN PATENT DOCUMENTS

| | | |
|---|---|---|
| EP | 408859 B1 | 1/1991 |
| EP | 671407 A2 | 9/1995 |
| WO | WO 90/13300 | 11/1990 |
| WO | WO 91/19502 | 12/1991 |
| WO | WO 92/01718 | 2/1992 |
| WO | WO 92/07572 | 5/1992 |
| WO | WO 94/26760 | 11/1994 |
| WO | WO 94/29477 | 12/1994 |
| WO | WO 95/00527 | 1/1995 |
| WO | WO 95/03059 | 2/1995 |
| WO | WO 95/29681 | 11/1995 |
| WO | WO 96/20204 | 7/1996 |
| WO | WO 96/25418 | 8/1996 |
| WO | WO 96/26950 | 9/1996 |
| WO | WO 97/01355 | 1/1997 |
| WO | WO 97/01569 | 1/1997 |
| WO | WO 97/14707 | 4/1997 |
| WO | WO 97/28173 | 8/1997 |
| WO | WO 97/28174 | 8/1997 |
| WO | WO 98/06730 | 2/1998 |
| WO | WO 99/42130 | 8/1999 |
| WO | WO 99/43353 | 9/1999 |
| WO | WO 99/43356 | 9/1999 |
| WO | WO 02/22820 | 3/2002 |
| WO | WO 02/062810 | 8/2002 |
| WO | WO 03/097658 | 11/2003 |
| WO | WO2004/058304 | 12/2003 |
| WO | WO 04/004636 | 1/2004 |
| WO | WO 05/054264 | 6/2005 |
| WO | WO2007/021721 | 8/2006 |
| WO | WO 06/127906 | 11/2006 |
| WO | WO 07/028050 | 3/2007 |
| WO | WO2008/100453 | 2/2008 |
| WO | WO-2008060378 A2 * | 5/2008 ............ C07H 15/207 |

OTHER PUBLICATIONS

Belcher, J.D. et al., "Inflammatory response in transgenic mouse models of human sickle cell anemia," Blood 96(11)Pt. 1 :600a, Abstract #2574, Nov. 16, 2000.

Berg et al., "A Carbohydrate Domain Common to Both Sialyl Le.sup.a and Sialyl Le.sup.x Is Recognized by the Endothelial Cell Leukocyte Adhesion Molecule ELAM-1," J. Biol. Chem. 266(23):14869-14872, 1991.

Berg et al., "The Cutaneous Lymphocyte Antigen Is a Skin Lymphocyte Homing Receptor for the Vascular Lectin Endothelial

(56) References Cited

OTHER PUBLICATIONS

Cell-Leukocyte Adhesion Molecule 1," J. Exp. Med. 174:1461-1466, 1991.
Bird et al., "Oligosaccharides Containing Fucose Linked .alpha.(1-3) and .alpha.(1-4) to N-Acetylglucosamine Cause Decompaction of Mouse Morulae," Devel. Biol. 104:449-460, 1984.
Bjercke,"Rational Design and Synthesis of Oligosaccharide Mimetics: Selectin Antagonists as Cell Adhesion Inhibitors," Abstracts of Papers, 210th ACS National Meeting, American Chemical Society, Chicago, IL, Aug. 20-24, 1995, MEDI-18.
Blanc-Muesser et al., "Syntheses Stereoselective de 1-Thioglycosides," Carbohydrate Research 67:305-328, 1978, and English Translation.
Bock, K. et al., "Conformations in Solution of a, a-Trehalose, a-D-Glucopyranosyl a-D-Mannopyranoside, and Their 1-Thioglycosyl Analogs, and a Tentative Correlation of Their Behaviour with Respect to the Enzyme Trehalase," European Journal of Biochemistry, 131:595-600, 1983.
Bowen et al., "Characterization of a Human Homologue of the Murine Peripheral Lymph Node Homing Receptor," Journal of Cell Biology, 109:421-427, 1989.
Brandley et al., "Carbohydrate Ligands of LEC Cell Adhesion Molecules," Cell, 63:861-863, 1990.
Broquet et al., "Effect of Desipramine on a Glycoprotein Sialyltransferase Activity in C6 Cultured Glioma Cells," J. Neurochem., 54:388-394, 1990.
Ceder, O. et al., "On the Absolute Configuration of 3-Cyclohexene-I-carboxylic Acid," Acta Chemica Scandivavica, 24(8):2693-2698, 1970.
Chemical Abstracts (STN), Accession No. 1997:584307, Jul. 8, 1997.
Childs et al. ,"High-molecular-weight glycoproteins are the major carriers of the carbohydrate differentiation antigens I, I and SSEA-1 of mouse teratocarcinoma cells," Biochem. J., 215:491-503 (1983).
Cleophax, J. et al., "A chiral synthesis of D-(+)-2,6-dideoxystreptamine and its microbial incorporation into novel antibodies," Journal of the American Chemical Society, 98 (22): 7110-7112 (Oct. 27, 1976).
Corral et al., "Requirements for Sialic Acid on Neutrophils in a GMP-140 (PADGEM) Mediated Adhesive Interaction with Activated Platelets," Biochem. Biophys. Res. Commun., 172:1349-1356, (1990).
Cumpstey, I. et al. "C2-Symmetrical Thiodigalactoside Bis-Benzamido Derivatives as High-Affinity Inhibitors of Galectin-3: Efficient Lectin Inhibition through Double Arginine—Arene Interactions," Angew Chem., 117:5240-5242 (2005).
Datta et al., "Isolation and purification of trehalose 6-mono- and 6,6'-di-corynomycolates from Cornyebacterium matruchotii. Structural characterization of .sup.1H NMR," Carbohydrate Research 245: 151-158, 1993.
Duijvestijn et al., "High Endothelial Differentiation in Human Lymphoid and Inflammatory Tissues Defined by Monoclonal Antibody HECA-452," Am. J. Path. 130:147-155, 1988.
Dupre et al., "Glycomimetic Selectin Inhibitors: (.alpha.-D-Mannopyranosyloxy)methylbiphenyls," Bioorganic & Medicinal Chemistry Letters 6(5): 569-572, 1996.
Edgington, "How Sweet It Is: Selectin-Mediating Drugs," Biotechnology 10: 383-389, 1992.
Eggens et al., "A Role of Carbohydrate-Carbohydrate Interaction in the Process of Specific Cell Recognition During Embryogenesis and Organogenesis: A Preliminary Note," Biochem. Biophys. Res. Commun. 158(3):913-920, 1989.
Eggens et al., "Specific Interaction between Le.sup.X and Le.sup.X Determinants. A Possible Basis for Cell Recognition in Preimplantation Embryos and in Embryonal Carcinoma Cells," J. Biol. Chem. 264(16):9476-9484, 1989.
Embury et al., "The contribution of endothelial cell P-selectin to the microvascular flow of mouse sickle erythrocytes in vivo," Blood 104(10):3378-3385, Nov. 15, 2004.
Ernst, "Substrate and donor specificity of glycosyl transferases," Glycoconjugate Journal 16: 161-170, 1999.
Fenderson et al., "A Multivalent Lacto-N-Fucopenataose III-Lysyllysine Conjugate Decompacts Preimplantation Mouse Embryos, While the Free Oligosaccharide is Ineffective," J. Exp. Med. 160:1591-1596, 1984.
Fenderson et al., "Coordinate Expression of X and Y Haptens during Murine Embryogenesis," Devel. Biol. 114:12-21, 1986.
Fenderson et al., "The blood group I antigen defined by monoclonal antibody C6 is a marker of early mesoderm during murine embryogenesis," Differentiation 38:124-133, 1988.
Fukushi et al., "Novel Fucolipids Accumulating in Human Adenocarcinoma," J. Biol. Chem. 259(16):10511-10517 (1984).
Fukushi et al., "Novel Fucolipids Accumulating in Human Adenocarcinoma. II. Selective Isolation of Hybridoma Antibodies That Differentially Recognize Mono-, Di-, and Trifucosylated Type 2 Chain," J. Biol. Chem. 259(7):4681-4685, 1984.
Gabius et al., "Endogenous Tumor Lectins: Overview and Perspectives," Anticancer Res. 6:573-578, 1986.
Gais, H.-J. et al., "Enantioselective and Enantioconvergent Syntheses of Building Blocks for the Total Synthesis of Cyclopentanoid Natural Products," Angewandte Chemie, Int. Ed. Eng. 23(2):142-143, 1984.
Gallatin et al., "A cell-surface molecule involved in organ-specific homing of lymphocytes," Nature 304:30-34, 1983.
Garber, N. et al., "On the specificity of the D-galactose-binding lectin (PA-I) of Pseudomonas aeruginosa and its strong binding to hydrophobic derivatives of D-galactose and thiogalactose," Biochimica et Biophysica Acta, 1116:331-333 (1992).
Gilboa-Gardner, N. et al., "A new mitogenic D-galactosephilic lectin isolated from seeds of the coral-tree Erythrina corallodendron. Comparison with Glycine max (soybean) and Pseudomonas aeruginosa lectins," Canadian Journal of Biochemistry, 59(5):315-320 (1981).
Gooi et al., "Stage-specific embryonic antigen involves alpha 1-3 fucosylated type 2 blood group chains," Nature 292:156-158, 1981.
Hakomori, "Aberrant Glycosylation in Cancer Cell Membranes as Focused on Glycolipids: Overview and Perspectives," Cancer Res. 45:2405-2414, 1985.
Hakomori et al., "Novel Fucolipids Accumulating in Human Adenocarcinoma. I. Glycolipids With Di- or Trifucosylated Type 2 Chain," J. Biol. Chem. 259(7):4672-4680, 1984.
Hakomori et al., "The Hapten Structure of a Developmentally Regulated Glycolipid Antigen (SSEA-1) Isolated From Human Erythrocytes and Adenocarcinoma: A Preliminary Note," Biochem. Biophys. Res. Comm. 100(4):1578-1586, 1981.
Handa et al., "Selectin GMP-140 (CD62; PADGEM) Binds to Sialosyl-Le$^a$ and Sialosyl-Le$^x$, and Sulfated Glycans Modulate this Binding," Biochemical and Biophysical Research Communication 181(3):1223-1230, 1991.
Hansson et al., "Biosynthesis of the Cancer-associated Sialyl-Le.sup.a Antigen," Journal of Biological Chemistry 260(16):9388-9392, 1985.
Harlan, "Introduction-anti-adhesion therapy in sickle cell disease," Blood 95:365-367, 2000.
Hasegawa et al., "Synthesis of deoxy-L-fucose-containing sialyl Lewis X ganglioside analogues," Carbohydrate Research 257: 67-80, 1994.
Hasegawa et al., "Synthesis of sialyl Lewis X ganglioside analogues containing modified L-fucose residues," Carbohydrate Research 274: 165-181, 1995.
Hebbel, P.R., "Blockade of Adhesion of Sickle Cells to Endothelium by Monoclonal Antibodies," The New England Journal of Medicine 342:1910-1912, Jun. 22, 2000.
Holmes et al., "Enzymatic Basis for the Accumulation of Glycolipids with X and Dimeric X Determinants in Human Lung Cancer Cells (NCI-H69)," J. Biol. Chem. 260(12):7619-7627, 1985.
Huse et al., "Generation of a Large Combinatorial Library of the Immunoglobulin Repertoire in Phage Lambda," Science 246:1275-1281, 1989.
Huwe, C. M. et al., "Design, Synthesis and Biological Evaluation of Aryl-substituted Sialyl Lewis X Mimetics Prepared Via Cross-metathesis of C-Fucopeptides," Biological & Medicinal Chemistry 7:773-788, 1999.

(56) References Cited

OTHER PUBLICATIONS

Hynes, R., "Integrins: A Family of Cell Surface Receptors," Cell 48:549-554, 1987.
Inwald, D. P. et al, "Platelet and leucocyte activation in childhood sickle cell disease: association with nocturnal hypoxaemia," British Journal of Haematologyl 11:474-481, Nov. 2000.
Issekutz, T., "Inhibition of in Vivo Lymphocyte Migration of Inflammation and Homing to Lymphoid Tissues by the TA-2 Monoclonal Antibody. A Likely Role for VLA-4 in Vivo," Journal of Immunology 147:4178-4184, 1991.
Itai, S. et al., "Differentiation-dependent Expression of I and Sialyl I Antigens in the Developing Lung of Human Embryos and in Lung Cancers," Cancer Research 50: 7603-7611, 1990.
Jeffrey et al., "Affinity Chromatography of Carbohydrate-Specific Immunoglobulins: Coupling of Oligosaccharides to Sepharose ," Biochem. Biophys. Res. Commun. 62:608-613, 1975.
Jentsch, K.D. et al., "Inhibition of Human Immunodeficiency Virus Type I Reverse Transcriptase by Suramin-related Compounds," The Journal of General Virology 68(8): 2183-2192, 1987.
Kaila, N. et al., "β-C-Mannosides as Selectin Inhibitors," Journal of Medicinal Chemistry 45(8): 1563-1566, 2002.
Kaila, N. et al., "Design and synthesis of sialyl Lewis(x) mimics as E- and P-selectin inhibitors," Med Res Rev 22(6):566-601, Nov. 2002.
Kannagi et al., "New Globoseries Glycosphingolipids in Human Teratocarcinoma Reactive with the Monoclonal Antibody Directed to a Developmentally Regulated Antigen, Stage-specific Embryonic Antigen 3," J. Biol. Chem. 258(14):8934-8942, 1983.
Kannagi et al., "Stage-specific embryonic antigens (SSEA-3 and -4) are epitopes of a unique globo-series ganglioside isolated from human teratocarcinoma cells," Embo J. 2(12):2355-2361, 1983.
Karaivanova et al., "Partial Characterization of Microsomal Sialyltransferase From Chicken Liver and Hepatoma Mc-29: II. Measurement of Enzyme Activities Utilizing Microsomal Glycoproteins as Exogenous Acceptors," Cancer Biochem. Biophys. 11:311-315, 1990.
Kaul, D.K. et al., "Hypoxia/reoxygenation causes inflammatory response in transgenic sickle mice but not in normal mice," The Journal of Clinical Investigation 106(3):411-420, Aug. 2000.
Kitagawa et al., "Characterization of Mucin-Type Oligosaccharides With the Sialyl-Le.sup.a Structure From Human Colorectal Adenocarcinoma Cells," Biochem. Biophys. Res. Commun. 178(3):1429-1436, 1991.
Kitagawa et al., "Immunoaffinity Isolation of a Sialyl-Le$^a$ Oligosaccharide from Human Milk," J. Biochem. 104:591-594, 1988.
Kneuer et al: "Selectins—potential pharmacological targets?" Drug Discovery Today vol. 11, No. 21-22, pp. 1034-1040, Oct. 2006.
Ko, HL et al. "In Vitro and In Vivo Inhibition of Lectin Mediated Adhesion of Pseudomonas aeruginosa by Receptor Blocking Carbohydrates," Infection, 15(4): 21-24 (1987).
Kogan, T.P. et al., "Novel Synthetic Inhibitors of Selectin-Mediated Cell Adhesion: Synthesis of 1,6-Bis[3-(3-carboxymethylphenyl)-r-(2-.alpha.-.sub.D-monnopyranosyloxy)p-henyl]hexane (TBC1269)," J Med. Chem 41:1099-1111, 1998.
Kogan, T.P. et al., "Rational Design and Synthesis of Small Molecule, Non-oligosaccharide Selectin Inhibitors: (.alpha.-D-Mannopyranosyloxy)biphenyl-Substituted Corboxylic Acids," J. Med. Chem. 38: 4976-4984, Dec. 22, 1995.
Kogan, T.P. et al., "Rational Design and Synthesis of Oligosaccharide Mimetics: Selectin Antagonists as Cell Adhesion Inhibitors," Abstracts of Papers, 210.sup.th ACS National Meeting, American Chemical Society, Chicago, IL, Aug. 20-24, 1995, MEDI-18.
Kohler et al., "Continuous cultures of fused cells secreting antibody of predefined specificity," Nature 256:495-497, 1975.
Kohler et al., "Derivation of specific antibody-producing tissue culture and tumor lines by cell fusion," Eur. J. Immunol. 6:511-519, 1976.
Kojima et al., "Specific Interaction between Gangliotriaosylceramide (G.sub.g3) and Sialosyllactosylceramide (G.sub.M3) as a Basis for Specific Cellular Recognition between Lymphoma and Melanoma Cells," J. Biol. Chem. 264(34):20159-20162, 1989.
Kolb et al., "Development of Tool for the Design of Selectin Antagonists," Chem. Eur. J. 3(10):1571-1578, 1997.
Kolb et al., "Recent progress in the glycodrug area," Pure & Applied Chemistry 69(9):1879-1884, 1997.
Koprowski et al., "Colorectal Carcinoma Antigens Detected by Hybridoma Antibodies," Somatic Cell Genetics 5(6):957-972, 1979.
Kuzuoka, "Antitumor activity of murine monoclonal antibody NCC-ST-421," Chem. Ab. 115:27344v, 1991.
Lamblin et al., "Primary Structure Determination of Five Sialylated Oligosaccharides Derived from Bronchial Mucus Glycoproteins of Patients Suffering from Cystic Fibrosis.," Journal of Biological Chemistry 259(14):9051-9058, 1984.
Lanne, B. et al., "Binding of the galactose-specific Pseudomonas aeruginose lectin, PA-I, to glycosphingolipids and other glycoconjugates," Glycoconjugate Journal, 11:292-298 (1994).
Larsen et al., "PADGEM-Dependent Adhesion of Platelets to Monocytes and Neutrophils is Mediated by a Lineage-Specific Carbohydrate, LNF III (CD15)," Cell 63:467-474, 1990.
Lindenberg et al., "Carbohydrate binding properties of mouse embryos," J. Reprod. Fert. 89:431-439, 1990.
Lipartiti et al., "Monosialoganglioside GM1 Reduces NMDA Neurotoxicity in Neonatal Rat Brain," Experimental Neurology 113:301-305, 1991.
Lowe et al., "A transfected human fucosyltransferase cDNA determines biosynthesis of oligosaccharide ligand(s) for endothelial-leukocyte adhesion molecule I," Biochem. Soc. Trans. 19(3):649-653, 1991.
Lowe et al., "ELAM-1-Dependent Cell Adhesion to Vascular Endothelium Determined by a Transfected Human Fucosyltransferase cDNA," Cell 63:475-484, 1990.
Macher et al., "A Novel Carbohydrate, Differentiation Antigen on Fucogangliosides of Human Myeloid Cells Recognized by Monoclonal Antibody VIM-2," Journal of Biological Chemistry 263(21):10186-10191, 1988.
Magnani et al., "A Monoclonal Antibody-defined Antigen Associated with Gastrointestinal Cancer Is a Ganglioside Containing Sialylated Lacto-N-fucopentaose II," Journal of Biological Chemistry 257(23):14365-14369, 1982.
Magnani et al., "Identification of the Gastrointestinal and Pancreatic Cancer-associated Antigen Detected by Monoclonal Antibody 19-9 in the Sera of Patients as a Mucin," Cancer Res. 43:5489-5492, 1983.
Magnani, J., "Carbohydrate Sequences Detected by Murine Monoclonal Antibodies," Chemistry and Physics of Lipids 42:65-74, 1986.
Magnani, J., "Potent Glycomimetic Inhibitors of the Adhesion Molecule, PA-IIL, for the Bacterial Pathogen, Pseudomonas auroginosa," Glycobiology 13(11): 854, Abstract No. 104, Oct. 2003.
Matsui, N. M. et al., "Heparin inhibits the flow adhesion of sickle red blood cells to Pselectin," Blood 100(10):3790-3796, Nov. 15, 2002.
Matsui, N. M. et al., "The Novel Adhesion of Erythrocytes to P-Selectin in Sickle Cell Disease," Blood 96(11) Pt. 1:600a, Abstract #2575, Nov. 16, 2000.
Matsui, N. M.et al., "P-selectin mediates the adhesion of sickle erythrocytes to the endothelium," Blood 98(6):1955-1962, Sep. 15, 2001.
Mitchell E. et al, "Structural basis for oligosaccharide-mediated adhesion of Pseudomonas aeruginosa in the lungs of cystic fibrosis patients," Nat. Struct. Biol. 9(12):918-921, 2002.
Mulligan et al., "Selection for animal cells that express the *Escherichia coli* gene coding for xanthine-gunine phosphoribosyltransferase," Proc. Natl. Acad. Sci. USA 78:2072-2076, 1981.
Nagel, R. L., "A Knockout of a Transgenic Mouse-Animal Models of Sickle Cell Anemia," The New England Journal of Medicine 339:194-195, Jul. 16, 1998.
Natarajan, M.M. et al., "Adhesion of sickle red blood cells and damage to interleukinlbeta stimulated endothelial cells under flow in vitro," Blood 87:4845-4852, 1996.

(56) References Cited

OTHER PUBLICATIONS

Nicolaou et al., "Total Synthesis of the Tumor-Associated Le$^x$ Family of Glycosphingolipids," J. Amer. Chem. Soc. 112:3693-3695, 1990.
Nudelman et al., "Novel Fucolipids of Human Adenocarcinoma: Disialosyl Lea Antigen (III.sup.4FucIII.sup.6NeuAcIV.sup.3NeuAcLc.sub.4) of Human Colonic Adenocarcinoma and the Monoclonal Antibody (FH7) Defining This Structure," J. Biol. Chem. 261:5487-5495,1986.
Orhlein, R., "Carbohydrates and Derivatives as Potential Drug Candidates with Emphasis on the Selectin and Linear-B Area," Mini Reviews in Medicinal Chemistry 1: 349-361, 2001.
Palcic et al., "A Bisubstrate Analog Inhibitor for .alpha.(1.fwdarw. 2)-Fucosyltransferase," J. Biol. Chem. 264:17174-17181, 1989.
Palcic et al., "Enzymic Synthesis of Oligosaccharides Terminating in the Tumor-Associated Sialyl-Lewis-a Determinant," Carbohydr. Res. 190:1-11, 1989.
Palcic et al., "Regulation of N-Acetylglucosaminyltransferase V Activity. Kinetic Comparisons of Parental, Rous Sarcoma Virus-Transformed BHK, and .sub.L-Phytohemagglutinin-Resistant BHK Cells Using Synthetic Substrates and an Inhibitory Substrate Analog," J. Biol. Chem. 265:6759-6769, 1990.
Palma-Vargas, J.M. et al., "Small-Molecule Selectin Inhibitor Protects Against Liver Inflammatory Response After Ischemia and Reperfusion," J. Am. Coll. Surg. 185: 365-372, 1997.
Perret, S. et al., "Structural basis for the interaction between human milk oligosaccharides and the bacterial lectin PA-IIL of Pseudomonas aeruginosa," Biochem. J. 389: 325-332, 2005.
Phillips et al., "ELAM-1 Mediates Cell Adhesion by Recognition of a Carbohydrate Ligand, Sialyl-Le.sup.x," Science 250:1130-1132, 1990.
Picker er al., "The Neutrophil Selectin LECAM-1 Presents Carbohydrate Ligands to the Vascular Selectins ELAM-1 and GMP-140," Cell 66:921-933, 1991.
Prokazova et al., "Sialylated lactosylceramides. Possible inducers of non-specific immunosuppression and atherosclerotic lesions," European Journal of Biochemistry 172:1-6, 1988.
Rauvala et al., "Studies on Cell Adhesion and Recognition. I. Extent and Specificity of Cell Adhesion Triggered by Carbohydrate-reactive Proteins (Glycosidases and Lectins) and by Fibronectin," J. Cell Biol. 88:127-137, 1981.
Rice et al., "An Inducible Endothelial Cell Surface Glycoprotein Mediates Melanoma Adhesion," Science 246:1303-1306, 1989.
Ruoslahti et al., "New Perspectives in Cell Adhesion: RGD and Integrins," Science 238:491-497, 1987.
Sakurai et al., "Selection of a Monoclonal Antibody Reactive with a High-Molecular-Weight Glycoprotein Circulating in the Body Fluid of Gastrointestinal Cancer Patients," Cancer Research 48:4053-4058, 1988.
Sastry et al., "Cloning of the immunological repertoire in *Escherichia coli* for generation of monoclonal catalytic antibodies: Construction of a heavy chain variable region-specific cDNA library," Proc. Natl. Acad. Sci. USA 86:5728-5732, 1989.
Scharfman et al., "Pseudomonas aeruginosa binds to neoglycoconjugates bearing mucin carbohydrate determinants and predominantly to sialyl-Lewis x conjugates," Glycobiology 9(8): 757-764, 1999.
Scharfman et al., "Recognition of Lewis x Derivatives Present on Mucins by Flagellar Components of Pseudomonas aeruginosa," Infection and Immunity 69(9): 5243-5248, Sep. 2001.
Schwizer et al. "Pre-organization of the Core Structure of E-Selectin Antagonist," Chemistry—A European Journal, 18(5): 1342-1351 (Jan. 2012).
Shitara et al., "Application of Anti-Sialyl Le.sup.a Monoclonal antibody, KM231, for Immunotherapy of Cancer," Anticancer Res. 11:2003-2014, 1991.
Siuzdak et al., "Examination of the Sialyl Lewis X—Calcium Complex by Electrospray Mass Spectrometry," Bioorganic & Medicinal Chemistry Letters 4(24): 2863-2866, 1994.

Solovey et al., "Circulating Activated Endothelial Cells in Sickle Cell Anemia," The New England Journal of Medicine 337:1584-1590, Nov. 27, 1997.
Solovey et al. "Modulation of endothelial cell activation in sickle cell disease: a pilot study," Blood, 97(7): 1937-1941 (Apr. 2001).
Sprengard et al., "Synthesis and Biological Activity of Novel Sialyl-Lewis.sup.X Conjugates," Bioorganic & Medicinal Chemistry Letters 6(5): 509-514, 1996.
Stanley et al., "The LEC11 Chinese Hamster Ovary Mutant Synthesizes N-Linked Carbohydrates Containing Sialylated, Fucosylated Lactosamine Units. Analysis by One- and Two-Dimensional H NMR Spectroscopy," J. Biol. Chem. 263(23):11374-11381, 1988.
Stephens et al.,"The construction of highly efficient and versatile set of mammalian expression vectors," Nucleic Acids Research. 17:7110, 1989.
Streeter et al., "Immunohistologic and Functional Characterization of a Vascular Addressin Involved in Lymphocyte Homing into Peripheral Lymph Nodes," Journal of Cell Biology 107: 1853-1862, 1988.
Stroud et al.,"Extended Type 1 Chain Glycosphingolipids: Dimeric Le.sup.a (III.sup.4V.sup.4Fuc.sub.2Lc.sub.6) as Human Tumor-associated Antigen," J. Biol. Chem. 266(13):8439-8446, 1991.
Svenson et al., "Coupling of Acid Labile Salmonella Specific Oligosaccharides to Macromolecular Carriers," J. Immunol. Meth. 25:323-335, 1979.
Takada et al., "Adhesion of Human Cancer Cells to Vascular Endothelium Mediated by a Carbohydrate Antigen, Sialyl Lewis A[1]," Biochem. Biophys. Res. Commun. 179(2):713-719, 1991.
Takeichi, "Cadherins: a molecular family essential for selective cell-cell adhesion and animal morphogenesis," Trends Genet. 3(8):213-217, 1987.
Thoma G. et al., "A readily Available, Highly Potent E-Selectin Antagonist," Angew. Chem. Int. Ed. 40(19): 3644-3647, 2001.
Thoma, G. et al., "Preorganization of the Bioactive Conformation of Sialyl Lewis$^X$ Analogues Correlates with Their Affinity to E-Selectin," Angew. Chem. Int. Ed. 40(10): 1941-1945, 2001.
Thoma, G. et al., "Synthesis and biological evaluation of a potent E-selectin antagonist," J. Med. Chem. 42 (23): 4909-4913, Nov. 18, 1999.
Thoma, G. et al., "Synthesis and Biological Evaluation of a Sialyl Lewis X Mimic with Significantly Improved E-selectin Inhibition," Bioorganic & Medicinal Chemistry Letters 11: 923-925, 2001.
Tilton, R.G., "Endotoxin-Induced Leukocyte Accumulation in Aqueous Fluid of Rats is Decreased by a Small Molecule Selectin," Investigative Opthalmology & Visual Science 37(3): S918, Abstract No. 4227, Feb. 15, 1996.
Trouet et al., "A covalent linkage between daunorubicin and proteins that is stable in serum and reversible by lysosomal hydrolases, as required for a lysosomotropic drug-carrier conjugate: In vitro and in vivo studies," Proc. Natl. Acad. Sci. USA 79:626-629, 1982.
Turhan, et al., "Primary role for adherent leukocytes in sickle cell vascular occlusion: A new paradigm," Proceedings of the National Academy of Sciences of the United States of America 99(5):3047-3051, Mar. 5, 2002.
Tyrrell, D. et al. "Structural requirements for the carbohydrate ligand of E-selectin," PNAS, 88: 10372-10376 (Nov. 1991).
Waldmann et al., "Synthesis of 2-Acetamindo-2-Deoxyglucosylasparagine Glyco-Tripeptide and -Pentapeptides by Selective C- and N-Terminal Elongation of the Peptide Chain," Carbohydrate Research 196: 75-93, 1990.
Walz et al., "Recognition by ELAM-1 of the Sialyl-Le.sup.X Determinant on Myeloid and Tumor Cells," Science 250:1132-1135, 1990.
Ward et al., "Blocking of adhesion molecules in vivo as anti-inflammatory therapy," Immunology 1: 165-171, 1994.
Whisler et al., "Regulation of Lymphocyte Responses by Human Gangliosides. I. Characteristics of Inhibitory Effects and the Induction of Impaired Activation," Journal of Immunology 125(5):2106-2111, 1980.
Winzer, K. et al. "The Pseudomonas aeruginosa Lectins PA-IL and PA-IIL are Controlled by Quorom Sensing and by RpoS," J. Bacteriol. 182(22): 6401-6411 (2000).

(56) References Cited

OTHER PUBLICATIONS

Yamazaki, F. et al,. "Synthesis of an appropriately protected core glycotetraoside, a key intermediate for the synthesis of 'bisected' complex-type glycans of a glycoprotein," Carbohydrate Research 201: 15-30, 1990.
Zhou et al., "The Selectin GMP-140 Binds to Sialylated, Fucosylated Lactosaminoglycans on Both Myeloid and Nonmyeloid Cells," Journal of Cell Biology 115(2):557-564, 1991.
Zopf et al., "Affinity Purification of Antibodies Using Oligosaccharide-Phenethylamine Derivatives Coupled to Sepharose," Meth. Enzymol. 50:171-175, 1978.
International Search Report and Written Opinion dated May 17, 2017, for corresponding International Application No. PCT/US2017/013929, filed Jan. 18, 2017.
Patton, J. et al., "Glycomimetic antagonists of the virulence factors of *P. aeruginosa* (Pa-IL and Pa-IIL) protect innate immune cells and increase the efficacy of antibiotic treatment in a chronic lung infection model," Pediatric Pulmonology 49:343-344, 2014.
Smith, T. et al., "Glycomimetic Compound GMI-1051 inhibits Pathogenic Functions of the Virulence Factor Lectins, Pa-II and Pa-IIL, from Pseudomonas aeruginosa," Glycobiology, 1142-1143, XP009194334, 2006.
Zarkowska, T., "Bio 2005 Annual International Convention: Exciting Developments in Glycotherapeutics," iDrugs 8(8):622-624, 2005.

\* cited by examiner

Compounds Used in Assays

Compound A

Glycomimetic Compound I

Percent survival following co-administration of saline (●), 40 mM glycomimetic compound (I) (▲), or 40 mM compound A (■) with $2\times10^6$ CFU of *P. aeruginosa* in the acute lung injury model Clinical disease score following co-administration of saline (●), 40 mM glycomimetic compound (I) (▲), or 40 mM compound A (■) with $2\times10^6$ CFU of *P. aeruginosa* in the acute lung injury model Percent survival following co-administration of saline, glycomimetic compound (I) (top panel), or compound A (bottom panel) with $1 \times 10^7$ CFU of *P. aeruginosa* in the acute lung injury model Clinical disease score following co-administration of saline, glycomimetic compound (I) (top panel), or compound A (bottom panel) with $1 \times 10^7$ CFU of *P. aeruginosa* in the acute lung injury model Percent survival following co-administration of saline, glycomimetic compound (I) (top panel), and compound A (bottom panel) with $1 \times 10^7$ CFU of *P. aeruginosa* in combination with tobramycin in the acute lung injury model Treatment protocol (A) and groups distribution (B) in monotherapy experiment Survival analysis, all the groups (A) different instillation time of glycomimetic compound (I) (B), comparison of glycomimetic compound (I) and compound A instilled at H4 p.i (C). Statistical analysis were performed for each group with the control infected group Weight loss analysis at H24 (A), H48 (B) and over time (C)

Score disease analysis at H24 (A), H48 (B) and over time (C)

Treatment protocol (A) and groups distribution (B) in tobramycin association study Survival analysis, all the groups(A), comparison of glycomimetic compound (I) and compound A instilled at H4 p.i (B), different instillation time of glycomimetic compound (I) (C). Statistical analysis were performed for each group with the control infected group Weight loss analysis over time (A), at H24 (B)

Score disease analysis over time (A), at H24 (B)

GLYCOMIMETIC INHIBITORS OF PA-IL AND PA-IIL LECTINS

Compounds, compositions, and methods for the diagnosis and/or treatment of diseases involving infections with and colonization by *Pseudomonas* bacteria including, for example, *Pseudomonas aeruginosa* in the lungs of patients with cystic fibrosis are disclosed herein. For example, glycomimetic compounds selective for binding PA-IL and/or PA-IIL lectins of *Pseudomonas* bacteria and compositions comprising at least one such agent are described.

*Pseudomonas* is an opportunistic bacterium that is responsible for infections in patients with compromised immune systems such as those with cystic fibrosis (CF). Cystic Fibrosis, a chronic lung disease that affects the respiratory, digestive and reproductive systems, is caused by mutations in the gene encoding the cystic fibrosis transmembrane conductance regulator (CFTR), which acts as a chloride channel.

The genetic mutations of CFTR which alter ion movements also affect the N-glycosylation of CFTR as well as other cell surface molecules. All of the exocrine glands of the patients are affected; however, the lungs are the primary site of morbidity and mortality. The general change in glycosylation is associated with an increase in infectivity by *Pseudomonas aeruginosa*. The salivary and respiratory mucins from CF patients also contain altered glycosylation patterns.

The major cause of morbidity and mortality in CF patients is chronic lung colonization by the bacterium, *Pseudomonas aeruginosa*, which results in pronounced lung infection with a robust neutrophilic inflammatory response leading to destruction of the lungs and death. Colonization by *Pseudomonas aeruginosa* initiates during the sessile phase of the bacteria in which virulence factors are secreted in concert. Two virulence factors that bind carbohydrates are lectins. These lectins, known as PA-IL and PA-IIL, bind these oligosaccharide structures with high affinity and represent a potential molecular target to block bacterial colonization.

Patients that are never fully colonized by the bacteria maintain an excellent long-term prognosis. Compounds that limit the colonization of *Pseudomonas* bacteria are known. See, e.g., U.S. Pat. Nos. 7,517,980 and 8,258,290. However, there remains a need for more effective compounds to provide better treatment.

The compounds of the present invention have a high affinity for binding to the PA-IL and/or PA-IIL lectins and may have a beneficial therapeutic effect on diseases, disorders, or conditions where inhibition of PAIL and/or PAIIL is useful, including CF. Furthermore, these compounds may be administered in combination with or conjugated to (i.e. attached directly or via a linker) a second therapeutic agent.

In some embodiments, at least one compound is chosen from:

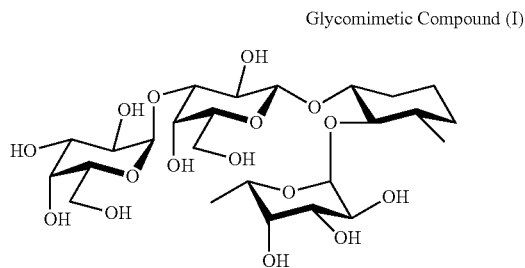

Glycomimetic Compound (I)

prodrugs thereof, and pharmaceutically acceptable salts of any of the foregoing.

As used herein, 'compound of Formula (I)' includes glycomimetic compound (I), pharmaceutically acceptable salts of glycomimetic compound (I), prodrugs of glycomimetic compound (I), and pharmaceutically acceptable salts of prodrugs of glycomimetic compound (I).

In some embodiments, pharmaceutical compositions comprising at least one compound of Formula (I) and at least one pharmaceutically acceptable carrier or diluent are disclosed.

In some embodiments, a method of inhibiting *Pseudomonas* bacteria infection in a subject is disclosed, the method comprising administering to the subject in need thereof an effective amount of at least one compound of Formula (I) or a pharmaceutical composition comprising at least one compound of Formula (I) and at least one pharmaceutically acceptable carrier or diluent.

In some embodiments, a method of detecting *Pseudomonas* bacteria is disclosed, the method comprising contacting a sample with a diagnostic agent conjugated to at least one compound of Formula (I) under conditions sufficient for the compound of Formula (I) to bind to the bacteria or its lectin products if present in the sample; and detecting the agent present in the sample, wherein the presence of the agent in the sample is indicative of the presence of *Pseudomonas* bacteria.

In some embodiments, a method of immobilizing *Pseudomonas* bacteria on a solid support comprising contacting, under conditions sufficient for binding, a sample containing *Pseudomonas* bacteria with at least one compound of Formula (I), wherein the at least one compound is immobilized on a solid support; and separating the sample from the solid support.

In some embodiments, the at least one compound of Formula (I) described herein may be used in the preparation of a medicament for the inhibition of *Pseudomonas* bacteria.

These and other aspects of the present invention will become apparent upon reference to the following detailed description and attached drawings. All references disclosed herein are hereby incorporated by reference in their entirety as if each was incorporated individually.

Figure 1:
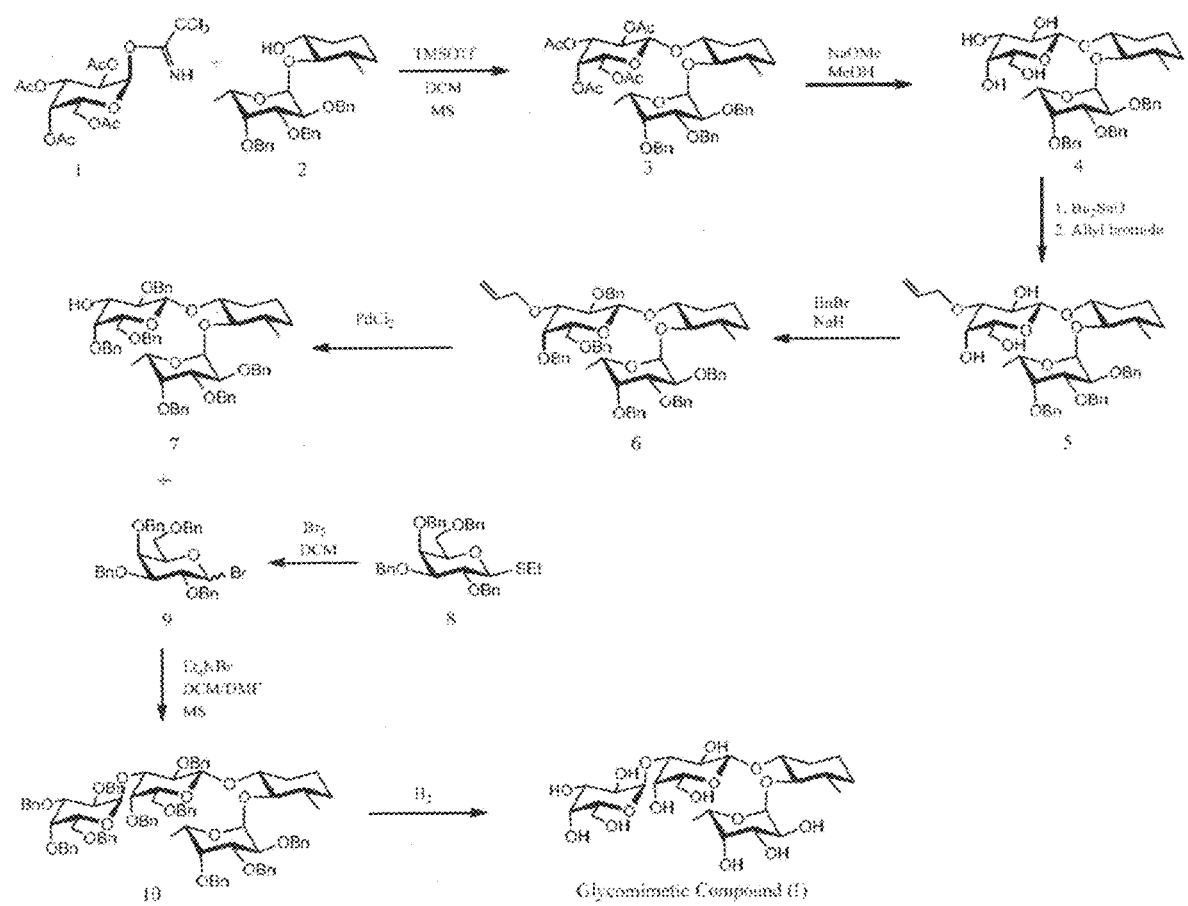
FIG. 1 is a diagram illustrating the synthesis of glycomimetic compound (I).
Figure 2:
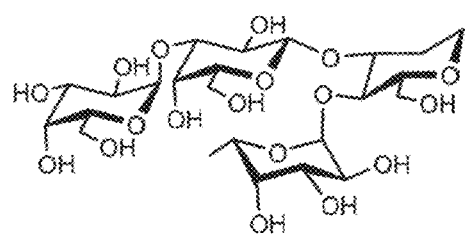
FIG. 2 depicts the structures of two of the compounds (compound A and glycomimetic compound (I)) used in one or more of the assays described herein.
Figure 2:
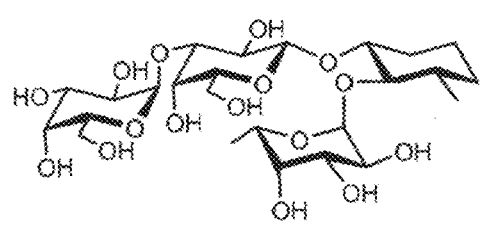

Disclosed herein are compounds and composition for treating and/or preventing at least one disease, disorder, and/or condition where inhibition of PAIL and/or PAIIL is useful. The compounds may have a variety of uses in vitro and in vivo.

In some embodiments, a method for the treatment and/or prevention of at least one disease, disorder, and/or condition where inhibition of PAIL and/or PAIIL is useful is disclosed, the method comprising administering to the subject in need thereof an effective amount of at least one compound chosen from:

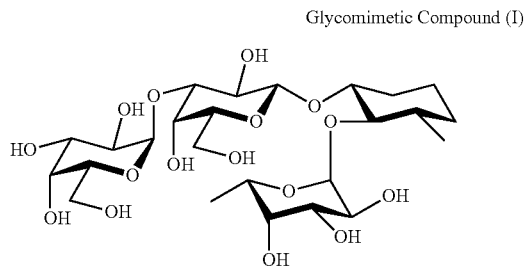

Glycomimetic Compound (I)

prodrugs thereof, and pharmaceutically acceptable salts of any of the foregoing.

In some embodiments, the at least one disease, disorder, and/or condition involves infections with and/or colonization by *Pseudomonas* bacteria. In some embodiments, the *Pseudomonas* bacteria are *Pseudomonas aeruginosa*. In some embodiments, the at least one disease, disorder, and/or condition is chosen from cystic fibrosis, ventilator-associated pneumonia, bronchiectasis, and chronic obstructive pulmonary disease. In some embodiments, the at least one disease, disorder, and/or condition is cystic fibrosis.

In some embodiments, a method for inhibiting infections with and/or colonization by *Pseudomonas* bacteria is disclosed, the method comprising administering to a subject in need thereof an effective amount of at least one compound of Formula (I) and/or a composition comprising at least one compound of Formula (I) and at least one pharmaceutically acceptable carrier or diluent. In some embodiments, the *Pseudomonas* bacteria are *Pseudomonas aeruginosa*.

In some embodiments, a method for treating cystic fibrosis is disclosed, the method comprising administering to a subject in need thereof an effective amount of at least one compound of Formula (I) and/or a composition comprising at least one compound of Formula (I) and at least one pharmaceutically acceptable carrier or diluent.

In some embodiments, at least one compound of Formula (I) may be administered in combination (i.e., simultaneously or sequentially) with a second therapeutic agent. In some embodiments, the second therapeutic agent is an anti-bacterial compound. In some embodiments, the at least one compound of Formula (I) may be administered in combination with tobramycin.

In some embodiments, at least one compounds of Formula (I) may also be used to target substances to *Pseudomonas* bacteria, (e.g., *Pseudomonas aeruginosa*). Such substances include therapeutic agents and diagnostic agents. Therapeutic agents may be a molecule, virus, viral component, cell, cell component or any other substance that may be demonstrated to modify the properties of a target cell so as to provide a benefit for treating or preventing a disease, disorder, and/or condition or regulating the physiology of a patient. A therapeutic agent may also be a drug or a prodrug that generates an agent having a biological activity in vivo. Molecules that may be therapeutic agents may be, for example, polypeptides, amino acids, nucleic acids, polynucleotides, nucleosides, steroids, polysaccharides or inorganic compounds. Such molecules may function in any of a variety of ways, including as enzymes, enzyme inhibitors, hormones, receptors, antisense oligonucleotides, catalytic polynucleotides, anti-viral agents, anti-tumor agents, anti-bacterial agents, immunomodulating agents and cytotoxic agents (e.g., radionuclides such as iodine, bromine, lead, rhenium, homium, palladium or copper). Diagnostic agents include imaging agents such as metals and radioactive agents (e.g., gallium, technetium, indium, strontium, iodine, barium, bromine and phosphorus-containing compounds), contrast agents, dyes (e.g., fluorescent dyes and chromophores) and enzymes that catalyze a colorimetric or fluorometric reaction. In some embodiments, the therapeutic and diagnostic agents may be attached to compounds of Formula (I). In some embodiments, said therapeutic and diagnostic agents are linked by an O glycosidic bond, a C glycosidic bond or an S glycosidic bond.

In some embodiments, at least one compound of Formula (I) may be immobilized on a solid support (such as linked to the interior surface of a tissue culture plate or other cell culture support) for use in immobilizing *Pseudomonas* bacteria or their products for screens, assays and growth in culture. Such linkage may be performed by any suitable technique. In some embodiments, at least one compound of Formula (I) may also be used to facilitate cell identification and sorting in vitro, permitting the selection of such bacterial cells. In some embodiments, the at least one compound of Formula (I) for use in such methods is linked to a diagnostic agent which is a detectable marker. Suitable markers are well known in the art and include radionuclides, luminescent groups, fluorescent groups, enzymes, dyes, constant immunoglobulin domains and biotin. In some embodiments, at least one compound of Formula (I) is linked to a fluorescent marker, such as fluorescein, is contacted with the cells, which are then analyzed by fluorescence activated cell sorting (FACS).

Such in vitro methods generally comprise contacting a sample (e.g., a biological preparation) with at least one compound of Formula (I) and detecting said compound of Formula (I) in the sample. If desired, one or more wash steps may be added to a method. For example, subsequent to contacting a sample with at least one compound of Formula (I) but prior to detection of said compound of Formula (I), the sample may be washed (i.e., contacted with a fluid and then removal of the fluid in order to remove unbound compound of Formula (I)). Alternatively, or in addition, a wash step may be added during the detection process. For example, if at least one compound of Formula (I) possesses a marker (a diagnostic agent) that may bind to a substance that is detectable, it may be desirable to wash the sample subsequent to contacting the sample with a detectable substance, but prior to the detection. As used herein, the phrase "detecting said compound of Formula (I) in the sample" includes detecting said compound of Formula (I) (or agent) while it is bound to the sample, or detecting said compound of Formula (I) (or agent) which was bound to the sample but after it has been separated from the sample.

Methods for Characterizing Compounds of Formula (I)

Biological activity of a compound described herein may be determined, for example, by performing at least one in vitro and/or in vivo study routinely practiced in the art and described herein or in the art. In vitro assays include without limitation binding assays, immunoassays, competitive binding assays and cell based activity assays.

Conditions for a particular assay include temperature, buffers (including salts, cations, media), and other components that maintain the integrity of any cell used in the assay and the compound, which a person of ordinary skill in the art will be familiar and/or which can be readily determined. A person of ordinary skill in the art also readily appreciates that appropriate controls can be designed and included when performing the in vitro methods and in vivo methods described herein.

The source of a compound that is characterized by at least one assay and techniques described herein and in the art may be a biological sample that is obtained from a subject who has been treated with the compound. The cells that may be used in the assay may also be provided in a biological sample. A "biological sample" may include a sample from a subject, and may be a blood sample (from which serum or plasma may be prepared), a biopsy specimen, one or more body fluids (e.g., lung lavage, ascites, mucosal washings, synovial fluid, urine), bone marrow, lymph nodes, tissue explant, organ culture, or any other tissue or cell preparation from the subject or a biological source. A biological sample may further include a tissue or cell preparation in which the morphological integrity or physical state has been disrupted, for example, by dissection, dissociation, solubilization, fractionation, homogenization, biochemical or chemical extraction, pulverization, lyophilization, sonication, or any other means for processing a sample derived from a subject or biological source.

As understood by a person of ordinary skill in the art, the terms, "treat" and "treatment," include medical management of a disease, disorder, or condition of a subject (i.e., patient, individual) (see, e.g., Stedman's Medical Dictionary). In general, an appropriate dose and treatment regimen provide at least one of the compounds of the present disclosure in an amount sufficient to provide therapeutic and/or prophylactic benefit. For both therapeutic treatment and prophylactic or preventative measures, therapeutic and/or prophylactic benefit includes, for example, an improved clinical outcome, wherein the object is to prevent or slow or retard (lessen) an undesired physiological change or disorder, to prevent or slow or retard (lessen) the expansion or severity of such disorder, or to ameliorate at least one symptom of the disorder. As discussed herein, beneficial or desired clinical results from treating a subject include, but are not limited to, abatement, lessening, or alleviation of symptoms that result from or are associated with the disease, condition, or disorder to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; and/or overall survival. "Treatment" can include prolonging survival when compared to expected survival if a subject were not receiving treatment.

A therapeutic result may relate, for example, to the prevention of lung infections. In some conditions, therapeutic results may be associated with the inhibition of *Pseudomonas* bacteria (such as *Pseudomonas aeruginosa*) or its products (where inhibiting includes, for example, arresting the growth of or killing the bacteria or preventing colonization by the bacteria).

In some embodiments of the methods described herein, the subject is a human. In some embodiments of the methods described herein, the subject is a non-human animal. Non-human animals that may be treated include mammals, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

The effectiveness of the compounds of the present disclosure in treating and/or preventing diseases, disorders, or conditions treatable by inhibiting PAIL and/or PAIIL can readily be determined by a person of ordinary skill in the relevant art. Determining and adjusting an appropriate dosing regimen (e.g., adjusting the amount of compound per dose and/or number of doses and frequency of dosing) can also readily be performed by a person of ordinary skill in the relevant art. One or any combination of diagnostic methods, including physical examination, assessment and monitoring of clinical symptoms, and performance of analytical tests and methods described herein, may be used for monitoring the health status of the subject.

Pharmaceutical Compositions and Methods of Using Pharmaceutical Compositions

Also provided herein are pharmaceutical compositions comprising at least one compound of Formula (I) and at least one pharmaceutically acceptable carrier or diluent.

In pharmaceutical dosage forms, any one or more of the compounds of the present disclosure may be administered in the form of a pharmaceutically acceptable derivative, such as a salt, and/or it/they may also be used alone and/or in appropriate association, as well as in combination, with other pharmaceutically active compounds.

An effective amount or therapeutically effective amount refers to an amount of at least one compound of the present disclosure or a pharmaceutical composition comprising at least one such compound that, when administered to a subject, either as a single dose or as part of a series of doses, is effective to produce at least one therapeutic effect and/or result. Optimal doses may generally be determined using experimental models and/or clinical trials. Design and execution of pre-clinical and clinical studies for each of the therapeutics (including when administered for prophylactic benefit) described herein are well within the skill of a person of ordinary skill in the relevant art. The optimal dose of a therapeutic may depend upon the body mass, weight, and/or blood volume of the subject. In some embodiments, the amount of at least one compound of Formula (I), that is present in a dose, may range from about 0.01 mg to about 100 mg per kg weight of the subject. The minimum dose that is sufficient to provide effective therapy may be used in some embodiments. Subjects may generally be monitored for therapeutic effectiveness using assays suitable for the disease or condition being treated or prevented, which assays will be familiar to those having ordinary skill in the art and are described herein. The level of a compound that is administered to a subject may be monitored by determining the level of the compound (or a metabolite of the compound) in a biological fluid, for example, in the blood, blood fraction (e.g., serum), and/or in the urine, and/or other biological sample from the subject. Any method practiced in the art to detect the compound, or metabolite thereof, may be used to measure the level of the compound during the course of a therapeutic regimen.

The dose of a compound described herein may depend upon the subject's condition, that is, stage of the disease, severity of symptoms caused by the disease, general health status, as well as age, gender, and weight, and other factors apparent to a person of ordinary skill in the medical art. Similarly, the dose of the therapeutic for treating a disease or disorder may be determined according to parameters understood by a person of ordinary skill in the medical art.

Pharmaceutical compositions may be administered in any manner appropriate to the disease or disorder to be treated as determined by persons of ordinary skill in the medical arts. An appropriate dose and a suitable duration and frequency of administration will be determined by such factors as discussed herein, including the condition of the patient, the type and severity of the patient's disease, the particular form of the active ingredient, and the method of administration. In general, an appropriate dose (or effective dose) and treatment regimen provides the composition(s) as described herein in an amount sufficient to provide therapeutic and/or prophylactic benefit (for example, an improved clinical outcome, such as more frequent complete or partial remissions, or longer disease-free and/or overall survival, or a lessening of symptom severity or other benefit as described in detail above).

The pharmaceutical compositions described herein may be administered to a subject in need thereof by any one of several routes that effectively delivers an effective amount of the compound. Non-limiting examples of suitable administrative routes include topical, oral, nasal, intrathecal, enteral, buccal, sublingual, transdermal, rectal, vaginal, intraocular, subconjuctival, sublingual, and parenteral administration, including subcutaneous, intravenous, intramuscular, intrasternal, intracavernous, intrameatal, and intraurethral injection and/or infusion.

The pharmaceutical compositions described herein may, for example, be sterile aqueous or sterile non-aqueous solutions, suspensions, or emulsions, and may additionally comprise at least one pharmaceutically acceptable excipient (i.e., a non-toxic material that does not interfere with the activity of the active ingredient). Such compositions may, for example, be in the form of a solid, liquid, or gas (aerosol). Alternatively, the compositions described herein may, for example, be formulated as a lyophilizate, or compounds described herein may be encapsulated within liposomes using technology known in the art. The pharmaceutical compositions may further comprise at least one additional pharmaceutically acceptable ingredient, which may be biologically active or inactive. Non-limiting examples of such ingredients include buffers (e.g., neutral buffered saline or phosphate buffered saline), carbohydrates (e.g., glucose, mannose, sucrose or dextrans), mannitol, proteins, polypeptides, amino acids (e.g., glycine), antioxidants, chelating agents (e.g., EDTA and glutathione), stabilizers, dyes, flavoring agents, suspending agents, and preservatives.

Any suitable excipient or carrier known to those of ordinary skill in the art for use in compositions may be employed in the compositions described herein. Excipients for therapeutic use are well known, and are described, for example, in *Remington: The Science and Practice of Pharmacy* (Gennaro, 21st Ed. Mack Pub. Co., Easton, Pa. (2005)). In general, the type of excipient may be selected based on the mode of administration, as well as the chemical composition of the active ingredient(s). Compositions may be formulated for the particular mode of administration. For parenteral administration, pharmaceutical compositions may further comprise water, saline, alcohols, fats, waxes, and buffers. For oral administration, pharmaceutical compositions may further comprise at least one component chosen, for example, from any of the aforementioned ingredients, excipients and carriers, such as mannitol, lactose, starch, magnesium stearate, sodium saccharine, talcum, cellulose, kaolin, glycerin, starch dextrins, sodium alginate, carboxymethylcellulose, ethyl cellulose, glucose, sucrose, and magnesium carbonate.

The pharmaceutical compositions (e.g., for oral administration or delivery by injection) may be in the form of a liquid. A liquid composition may include, for example, at least one the following: a sterile diluent such as water for injection, saline solution, physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral preparation can be enclosed in ampoules, disposable syringes or multiple dose vials made of glass or plastic. In some embodiments, the pharmaceutical composition comprises physiological saline. In some embodiments, the pharmaceutical composition is an injectable composition, and in some embodiments, the injectable composition is sterile.

For oral formulations, at least one of the compounds of the present disclosure can be used alone or in combination with at least one additive appropriate to make tablets, powders, granules and/or capsules, for example, those chosen from conventional additives, disintegrators, lubricants, diluents, buffering agents, moistening agents, preservatives, coloring agents, and flavoring agents. The pharmaceutical compositions may be formulated to include at least one buffering agent, which may provide for protection of the active ingredient from low pH of the gastric environment and/or an enteric coating. A pharmaceutical composition may be formulated for oral delivery with at least one flavoring agent, e.g., in a liquid, solid or semi-solid formulation and/or with an enteric coating.

Oral formulations may be provided as gelatin capsules, which may contain the active compound or biological along with powdered carriers. Similar carriers and diluents may be used to make compressed tablets. Tablets and capsules can be manufactured as sustained release products to provide for continuous release of active ingredients over a period of time. Compressed tablets can be sugar coated or film coated to mask any unpleasant taste and protect the tablet from the atmosphere, or enteric coated for selective disintegration in the gastrointestinal tract.

A pharmaceutical composition may be formulated for sustained or slow release. Such compositions may generally be prepared using well known technology and administered by, for example, oral, rectal or subcutaneous implantation, or by implantation at the desired target site. Sustained-release formulations may contain the active therapeutic dispersed in a carrier matrix and/or contained within a reservoir surrounded by a rate controlling membrane. Excipients for use within such formulations are biocompatible, and may also be biodegradable. In some embodiments, the formulation provides a relatively constant level of active component release. The amount of active therapeutic contained within a sustained release formulation depends upon the site of implantation, the rate and expected duration of release, and the nature of the condition to be treated or prevented.

The pharmaceutical compositions described herein can be formulated as suppositories by mixing with a variety of bases such as emulsifying bases or water-soluble bases. The pharmaceutical compositions may be prepared as aerosol formulations to be administered via inhalation. The pharmaceutical compositions may be formulated into pressurized acceptable propellants such as dichlorodifluoromethane, propane, nitrogen and the like.

The compounds of the present disclosure and pharmaceutical compositions comprising these compounds may be administered topically (e.g., by transdermal administration). Topical formulations may be in the form of a transdermal patch, ointment, paste, lotion, cream, gel, and the like. Topical formulations may include one or more of a penetrating agent or enhancer (also call permeation enhancer), thickener, diluent, emulsifier, dispersing aid, or binder. Physical penetration enhancers include, for example, electrophoretic techniques such as iontophoresis, use of ultrasound (or "phonophoresis"), and the like. Chemical penetration enhancers are agents administered either prior to, with, or immediately following administration of the therapeutic, which increase the permeability of the skin, particularly the stratum corneum, to provide for enhanced penetration of the drug through the skin. Additional chemical and physical penetration enhancers are described in, for example, Transdermal Delivery of Drugs, A. F. Kydonieus (ED) 1987 CRL Press; Percutaneous Penetration Enhancers, eds. Smith et al. (CRC Press, 1995); Lenneras et al., *J. Pharm. Pharmacol.* 54:499-508 (2002); Karande et al., *Pharm. Res.* 19:655-60 (2002); Vaddi et al., *Int. J. Pharm.* 91:1639-51 (2002); Ventura et al., *J. Drug Target* 9:379-93 (2001); Shokri et al., *Int. J. Pharm.* 228(1-2):99-107 (2001); Suzuki et al., *Biol. Pharm. Bull.* 24:698-700 (2001); Alberti et al., *J. Control Release* 71:319-27 (2001); Goldstein et al., *Urology* 57:301-5 (2001); Kiijavainen et al., *Eur. J. Pharm. Sci.* 10:97-102 (2000); and Tenjarla et al., *Int. J. Pharm.* 192: 147-58 (1999).

Kits comprising unit doses of at least one compound of the present disclosure, for example in oral or injectable doses, are provided. Such kits may include a container comprising the unit dose, an informational package insert describing the use and attendant benefits of the therapeutic in treating the pathological condition of interest, and/or optionally an appliance or device for delivery of the at least one compound of Formula (I) and/or pharmaceutical composition comprising the same.

EXAMPLES

Example 1

Synthesis of Glycomimetic Compound (I)

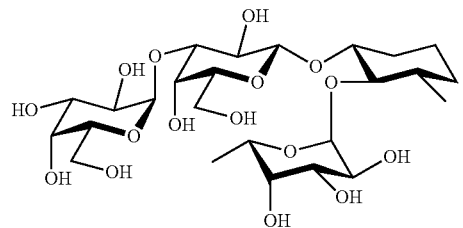

Synthesis of Compound 3:

Compound 2 (WO 2008/060378 (published May 22, 2008)) (8.12 g, 14.8 mmol) was dissolved in methylene chloride (200 mL). Flame dried 4 Å molecular sieves (18 g) were added and the mixture was cooled to −40° C. Trimethylsilyl triflate (0.4 mL, 2.23 mmol) was added. After stirring 10 minutes, a solution of compound 1 (9.513 g, 19.31 mmol) dissolved in methylene chloride (95 mL) was added dropwise via a syringe pump over 5 hours. Upon complete addition, the reaction mixture was quenched by addition of trimethylamine (4.14 mL, 29.7 mmol) at −40° C. After stirring 10 minutes the reaction mixture was filtered through Celite and the filtrate concentrated. The reaction mixture was separated via Combiflash using a 220 g silica cartridge and eluting with a gradient from 0-50% EtOAc/ hexanes to afford compound 3 (10.09 g) as a colorless foam. HPLC (Z50NP) $t_R$=5.44 min (89%).

HPLC (Z50NP) conditions: Agilent 1100 HPLC. Zorbax Eclipse XDB-C18, 50×4.6 mm 1.8 micron column. Solvent A Water (0.1% TFA); Solvent B Acetonitrile (0.07% TFA), Gradient 5 min 95% A to 95% B; 1 min hold at 95% B; 1 min recycle back to 95% A; 30 sec hold. UV Detection @ 210 and 254 nm with no reference.

Synthesis of Compound 4:

Compound 3 (10.0 g, 11.4 mmol) was dissolved in methanol and cooled on an ice bath. Sodium methoxide (3.5 equivalents) was added and the reaction mixture was stirred overnight allowing it to warm to room temperature. The reaction mixture was neutralized by addition of Dowex acidic ion exchange resin. The resin was removed by filtration. The solvent was removed and the crude material was used without further purification. $^1$H NMR (300 MHz, CDCl$_3$) δ 7.48-7.19 (m, 15H), 5.18 (d, J=3.3 Hz, 1H), 4.98 (d, J=11.4 Hz, 1H), 4.85 (d, J=11.4 Hz, 1H), 4.80 (d, J=1.3 Hz, 2H), 4.75 (d, J=11.5 Hz, 1H), 4.66 (q, J=6.0 Hz, 1H), 4.62 (d, J=11.3 Hz, 1H), 4.34-4.27 (m, 1H), 4.11 (dd, J=10.3, 3.3 Hz, 1H), 4.05 (dd, J=10.2, 2.4 Hz, 1H), 3.90 (broad s, 1H), 3.87 (dd, J=6.2, 2.6 Hz, 1H), 3.80-3.66 (m, 3H), 3.58-3.53 (m, 2H), 3.45-3.38 (m, 1H), 3.30 (t, J=9.3 Hz, 1H), 3.16 (d, J=1.4 Hz, 1H), 3.09 (dd, J=8.5, 4.2 Hz, 1H), 3.01 (d, J=2.7 Hz, 1H), 2.90 (d, J=2.1 Hz, 1H), 2.16-2.05 (m, 1H), 1.71-1.57 (m, 4H), 1.41-1.18 (m, 2H), 1.14 (d, J=6.5 Hz, 3H), 1.11 (d, J=6.3 Hz, 3H), 1.02 (m, 1H).

Synthesis of Compound 5:

Dibutyloxostannane (0.7305 g, 2.934 mmol) was added to a solution of compound 4 (1.60 g, 2.26 mmol) in methanol (12.0 mL) and the slurry was stirred at reflux for 4 hours. The reaction mixture became homogeneous after about 1 hour. The reaction mixture was cooled to room temperature then concentrated and azeotroped with toluene (2×). The crude material was dissolved in toluene (12.0 mL). Allyl bromide (0.3906 mL, 4.514 mmol) was added followed by tetra-N-butylammonium iodide (0.5419 g, 1.467 mmol). The reaction mixture was stirred 1 hour at 70° C. Additional tetra-N-butylammonium iodide (0.2918 g, 0.7900 mmol) and allyl bromide (0.40 mL, 4.6 mmol) were added and the reaction mixture was stirred overnight at 70° C. The reaction mixture was concentrated and then the residue adsorbed onto silica gel. The reaction mixture was separated by combiflash (40 g column) eluting with a gradient of 0-100% EtOAc in hexanes to afford Compound 5 as a red oil. HPLC (Z50NP) $t_R$=4.675 min (100%). $^1$H NMR (300 MHz, CDCl$_3$) δ 7.45-7.22 (m, 15H), 5.95 (ddt, J=17.3, 10.3, 5.7 Hz, 1H), 5.33 (dq, J=17.2, 1.6 Hz, 1H), 5.23 (dq, J=10.3, 1.3 Hz, 1H), 5.14 (d, J=3.1 Hz, 1H), 4.97 (d, J=11.5 Hz, 1H), 4.86 (d, J=11.6 Hz, 1H), 4.81 (d, J=2.7 Hz, 1H), 4.77 (d, J=11.6 Hz, 1H), 4.71 (q, J=6.4 Hz, 1H), 4.62 (d, J=11.5 Hz, 1H), 4.30 (d, J=7.7 Hz, 1H), 4.21 (dt, J=5.8, 1.4 Hz, 2H), 4.09 (dd, J=4.3, 2.8 Hz, 2H), 4.00 (dd, J=3.4, 1.2 Hz, 1H), 3.89 (dd, J=11.5, 6.4 Hz, 1H), 3.80-3.67 (m, 3H), 3.66 (t, J=6.0 Hz, 1H), 3.42 (dd, J=6.4, 5.0 Hz, 1H), 3.38-3.25 (m, 3H), 2.78 (s, 1H), 2.63 (s, 1H), 2.16-2.07 (m, 1H), 1.81-1.46 (m, 2H), 1.42-1.19 (m, 2H), 1.15 (d, J=6.4 Hz, 3H), 1.14-1.07 (m, 4H), 1.07-0.96 (m, 1H).

Synthesis of Compound 6:

Sodium Hydride (60% in mineral oil, 0.921 g, 23.0 mmol) was added to N,N-dimethylformamide (20.0 mL) and the resulting slurry cooled on an ice bath. A solution of compound 5 (3.45 g, 4.61 mmol) in N,N-dimethylformamide (15.0 mL) was added dropwise over 10 minutes. After stirring for 30 minutes on the ice bath, benzyl bromide (2.46 mL, 20.7 mmol) was added and stirring continued. After 2 hours the reaction mixture was quenched by the addition of methanol (2 mL). The reaction mixture was diluted with sat. NH$_4$Cl solution (50 mL) and water (25 mL) and transferred to a separatory funnel. The mixture was extracted with dichloromethane (3×). The combined organic phases were washed with sat. NaHCO$_3$ solution, brine, dried, and then concentrated. The residue was adsorbed onto silica gel and purified by combiflash using a 40 g silica cartridge and eluting with a gradient of 0-30% EtOAc in hexanes to afford Compound 6 as a white foam. HPLC (Z50NP) $t_R$=6.824 min (100%). $^1$H NMR (300 MHz, CDCl$_3$) δ 7.47-7.12 (m, 30H), 5.98 (dtt, J=17.3, 10.3, 5.7 Hz, 1H), 5.36 (dq, J=17.1, 1.7 Hz, 1H), 5.20 (dq, J=9.0, 1.3, 1H), 5.02 (d, J=3.3 Hz, 1H), 4.95 (dd, J=10.7, 4.6 Hz, 2H), 4.86 (q, J=6.4 Hz, 1H), 4.81 (d, J=11.7 Hz, 1H), 4.72 (d, J=11.3 Hz, 2H), 4.68-4.55 (m, 3H), 4.52 (d, J=8.1 Hz, 1H), 4.44 (m, 4H), 4.27-4.23 (m, 2H), 4.06 (d, J=11.4 Hz, 1H), 4.01-3.94 (m, 3H), 3.73 (t, J=8.8 Hz, 1H), 3.68-3.57 (m, 3H), 3.52 (dd, J=8.7, 4.7 Hz, 1H), 3.44 (dd, J=9.7, 2.9 Hz, 1H), 3.30 (s, 1H), 3.25 (t, J=9.4 Hz, 1H), 2.12 (broad d, J=12.0 Hz, 1H), 1.69-1.60 (m, 4H), 1.43-1.17 (m, 2H), 1.10 (d, J=6.5 Hz, 3H), 1.06-0.94 (m, 1H).

Synthesis of Compound 7:

Palladium (II) chloride (43.5 mg, 0.245 mmol) was added to a stirred solution of compound 6 (1.00 g, 0.981 mmol) in methanol (10 mL) and methylene chloride (5 mL) at room temperature. The mixture was stirred for 2 hours. The mixture was filtered through Celite and triethyl amine (1 mL) was added before concentration. The green residue was adsorbed onto silica gel (buffered with 10% triethylamine) and purified by combiflash using a 12 g silica cartridge and eluting with a gradient of 0-40% EtOAc in hexanes to afford Compound 7 as a white foam. HPLC (Z50NP) $t_R$=6.273 min (100%). MS data calculated for $C_{61}H_{70}O_{11}$: 1002.3 (M+Na, positive mode). $^1$H NMR (300 MHz, CDCl$_3$) δ 7.48-7.13 (m, 30H), 5.09 (d, J=11.2 Hz, 1H), 5.04 (d, J=3.3 Hz, 1H), 4.85 (d, J=10.8 Hz, 1H), 4.84 (q, J=6.0 Hz, 1H), 4.82 (d, J=11.9 Hz, 1H), 4.73 (d, J=11.7 Hz, 1H), 4.70-4.64 (m, 2H), 4.64-4.58 (m, 2H), 4.56 (d, J=10.6 Hz, 1H), 4.49 (d, J=10.6 Hz, 1H), 4.49-4.38 (m, 2H), 4.16 (d, J=11.4 Hz, 1H), 4.06-3.93 (m, 3H), 3.77-3.52 (m, 5H), 3.39-3.35 (m, 1H), 3.26 (t, J=9.4 Hz, 1H), 2.39 (d, J=3.7 Hz, 1H), 2.14 (broad d, J=12.1 Hz, 1H), 1.71-1.64 (m, 2H), 1.42-1.16 (m, 2H), 1.12 (d, J=9.0 Hz, 3H), 1.11 (d, J=6.0 Hz, 3H), 1.08-0.95 (m, 1H).

Synthesis of Compound 10:

Bromine (0.081 mL, 1.583 mmol) was added dropwise to a stirred solution of ethyl 2,3,4,6-tetra-O-benzyl-1-thio-hexopyranoside (compound 8; Carbosynth cat #ME05429) (0.8958 g, 1.532 mmol) in methylene chloride (2.03 mL, 31.6 mmol) at 0° C. for 45 minutes. Cyclohexene (0.1810 mL, 1.787 mmol) was added and stirring continued for another 15 minutes to afford a solution of compound 9.

In a separate flask tetra-N-butylammonium bromide (0.6584 g, 2.042 mmol), 4 Å MS (1.4 g), and 2,6-lutidine (0.2366 mL, 2.042 mmol) were added to a solution of Compound 7 (0.500 g, 0.511 mmol) in methylene chloride (3.7 mL) and N,N-dimethylformamide (3.7 mL) at room temperature and stirred for 1 h. The solution of compound 9 was added in one portion and the resulting reaction mixture was stirred 2 days at room temperature. The mixture was filtered through Celite. The filtrate was concentrated and the residue adsorbed onto silica gel treated with triethylamine (10%). The crude product was purified by combiflash using a 12 g silica cartridge and eluting with a gradient of 0-30% EtOAc in hexanes to afford compound 10 as a white foam. HPLC (Z50P) $t_R$=6.750 min (93%). MS data calculated for $C_{61}H_{70}O_{11}$: 1524.4 (M+Na, positive mode). $^1$H NMR (300 MHz, CDCl$_3$) δ 7.54-7.09 (m, 50H), 5.31 (d, J=3.3 Hz, 1H), 5.11 (d, J=7.0 Hz, 1H), 5.09-5.03 (m, 2H), 4.97 (d, J=11.5 Hz, 1H), 4.94-4.83 (m, 3H), 4.80 (s, 1H), 4.79 (d, J=2.2 Hz, 1H), 4.77-4.69 (m, 1H), 4.69-4.55 (m, 5H), 4.51 (d, J=7.6 Hz, 2H), 4.43-4.33 (m, 3H), 4.30 (d, J=3.3 Hz, 2H), 4.21 (dd, J=10.2, 3.3 Hz, 1H), 4.09 (d, J=2.7 Hz, 1H), 4.06 (d, J=1.9 Hz, 2H), 4.04-3.93 (m, 3H), 3.86 (dd, J=10.0, 2.5 Hz, 1H), 3.82-3.70 (m, 3H), 3.65 (dt, J=8.5, 4.2 Hz, 1H), 3.61-3.48 (m, 2H), 3.36-3.22 (m, 3H), 2.09 (broad d, J=13.4 Hz, 1H), 1.83 (s, 1H), 1.73-1.58 (m, 3H), 1.40-1.20 (m, 3H), 1.17 (d, J=6.4 Hz, 3H), 1.15 (d, J=6.4 Hz, 3H), 1.11-1.01 (m, 1H).

HPLC (Z50P) conditions: Agilent 1100 HPLC. Zorbax Eclipse XDB-C18, 50×4.6 mm 1.8 micron column. Solvent A Water (0.1% TFA); Solvent B Acetonitrile (0.07% TFA), Gradient 3 min 95% A to 100% B; 4 min hold at 100% B; 1 min recycle back to 95% A; 30 sec hold. UV Detection @ 210 and 254 nm with no reference.

Synthesis of Glycomimetic Compound (I):

Palladium hydroxide (20% Pd(OH)$_2$ on C 50% wet, 0.216 g, 0.154 mmol) was added to a degassed solution of compound 10 (0.425 g, 0.283 mmol) in methanol (23 mL) and 1,4-dioxane (2.32 mL) with a drop of water. The reaction mixture was stirred under a hydrogen atmosphere at room temperature overnight. The mixture was filtered through Celite and the cake washed with methanol. The combined filtrates were concentrated and then dissolved in DMF (1 mL, some heating required). The residue was purified by loading the DMF onto a combiflash gold column (4 g) and pulling a vacuum on it to remove the DMF. This was then attached to another 4 g combiflash column and eluted on the combiflash unit with a gradient of 0-50% MeOH in DCM to afford glycomimetic compound (I) as a white solid. MS data calculated for $C_{25}H_{44}O_{16}$: 623.4 (M+Na, positive mode); 599.3 (M-H, negative mode). $^1$H NMR (400 MHz, $D_2O$): δ 5.03 (s, 1H), 4.98 (s, 1H), 4.77 (q, J=6.8 Hz, 1H), 4.41 (d, J=7.9 Hz, 1H), 4.09 (t, J=6.6 Hz, 1H), 4.05 (s, 2H), 3.89 (s, 1H), 3.84 (d, J=10.7 Hz, 1H), 3.78 (d, J=10.7 Hz, 1H), 3.75-3.68 (m, 2H), 3.68-3.56 (m, 9H), 3.51 (d, J=8.5 Hz, 1H), 3.49-3.44 (m, 1H), 3.11 (t, J=9.6 Hz, 1H), 2.04-1.97 (m, 1H), 1.61-1.41 (m, 3H), 1.16 (q, J=11.9 Hz, 2H), 1.06 (d, J=6.2 Hz, 3H), 0.97 (d, J=6.3 Hz, 3H).

Example II

Assay for PA-IL Antagonist Activity

Wells of a microtiter plate (plate 1) are coated with PA-IL (Sigma-Aldrich, St. Louis, Mo.) by incubation for 2 hrs at 37° C. The wells are then blocked for 2 hrs by the addition of 1% bovine serum albumin (BSA) diluted in TBS-Ca (50 mM TrisHCl, 150 mM NaCl, 2 mM $CaCl_2$) pH 7.4) mixed 1:1 v/v with Stabilcoat (Surmodics, Eden Prairie, Minn.). In a second low-binding round-bottom microtiter plate (plate 2), test antagonists are serial diluted in 1% BSA in TBS-Ca/Stabilcoat (60 µl/well). Preformed conjugates of α-galactose-PAA-biotin (GlycoTech Corp, Gaithersburg, Md.) mixed with streptavidin-HRP (KPL Labs, Gaithersburg, Md.) are added to each well of plate 2 (60 µl/well of 2 µg/ml). Plate 1 is then washed with TBS-Ca and 100 µl/well are transferred from plate 2 to plate 1. After incubation at room temperature for 2 hrs, plate 1 is washed and 100 µl of TMB reagent (KPL Labs, Gaithersburg, Md.) is added to each well. After incubation for 5 minutes at room temperature, the reaction is stopped by adding 100 µl/well of 1M $H_3PO_4$ and the absorbance of light at 450 nm is determined by a microtiter plate reader. Absorbance is plotted as a function of antagonist concentration and the concentration at which 50% maximal absorbance (IC50) is obtained is determined from the plot.

| Compound | IC50 (µM) |
|---|---|
| Compound A | 14.1 |
| Glyco Cmp (I) | 7.2 |

Example III

Assay for PA-IIL Antagonist Activity

Wells of a microtiter plate (plate 1) are coated with PA-IIL (Dr. Wimmerova, Masaryk University, Brno, Czech Republic) by incubation for 2 hrs at 37° C. The wells are then blocked for 2 hrs by the addition of 1% bovine serum albumin (BSA) diluted in TBS-Ca (50 mM TrisHCl, 150 mM NaCl, 2 mM $CaCl_2$ pH 7.4) mixed 1:1 v/v with Stabilcoat (Surmodics, Eden Prairie, Minn.). In a second low-binding round-bottom microtiter plate (plate 2), test antagonists are serial diluted in 1% BSA in TBS-Ca/Stabilcoat (60 µl/well). Preformed conjugates of fucose-PAA-biotin (GlycoTech Corp, Gaithersburg, Md.) mixed with streptavidin-HRP (KPL Labs, Gaithersburg, Md.) are added to each well of plate 2 (60 µl/well of 2 µg/ml). Plate 1 is then washed with TBS-Ca and 100 µl/well are transferred from plate 2 to plate 1. After incubation at room temperature for 2 hrs, plate 1 is washed and 100 µl of TMB reagent (KPL Labs, Gaithersburg, Md.) is added to each well. After incubation for 5 minutes at room temperature, the reaction is stopped by adding 100 µl/well of 1M $H_3PO_4$ and the absorbance of light at 450 nm is determined by a microtiter plate reader. Absorbance is plotted as a function of antagonist concentration and the concentration at which 50% maximal absorbance (IC50) is obtained is determined from the plot.

| Compound | IC50 (µM) |
|---|---|
| Compound A | 0.42 |
| Glyco Cmp (I) | 0.44 |

Example IV

Acute Lung Injury Model

Cohorts of male BalB/c mice (n=5/group) were infected intranasally with either a low ($1-2\times10^6$ CFU) or a high ($1-2\times10^7$ CFU) inoculum of *Pseudomonas aeruginosa* strain PaO, in combination with saline or multiple dose levels (8 nM, 20 nM and 40 nM, corresponding to 10, 25 and 50 mg/kg, respectively) of glycomimetic compound (I) or compound A. The bacteria were coadministered with glycomimetic compound (I) or compound A directly into the lungs of each mouse by intratracheal (i.t.) injection via the oropharynx using a 24-gauge feeding needle (total volume of 0.05 mL).

Clinical Scores.

Figure 4:
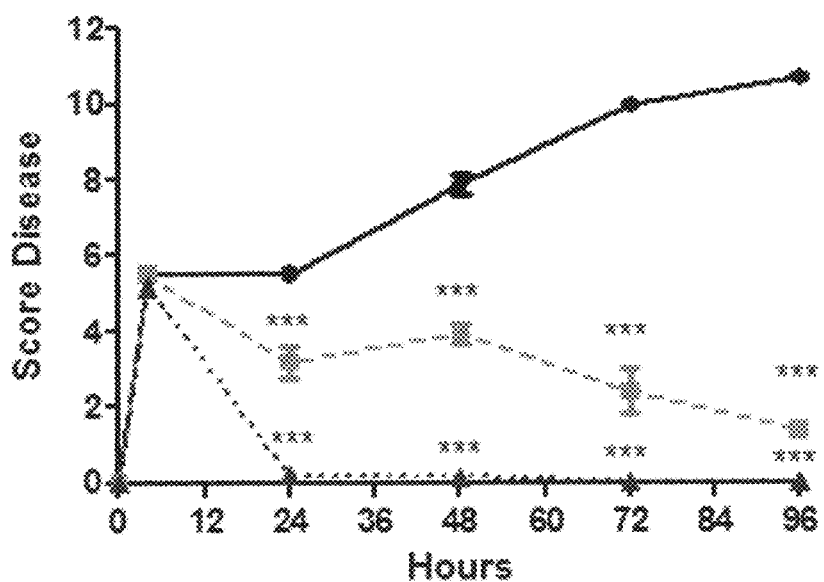
FIG. 4 depicts the clinical disease score following co-administration of saline, glycomimetic compound (I), or compound A with $2\times10^6$ CFU of *Pseudomonas aeruginosa* in the acute lung injury model.
Figure 6:
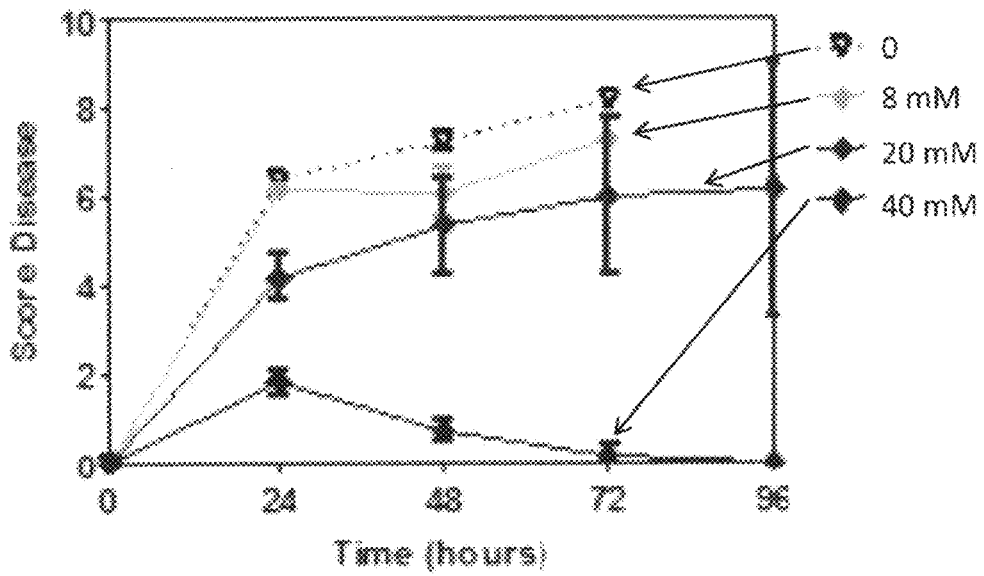
FIG. 6 depicts the clinical disease score following co-administration of saline, glycomimetic compound (I), or compound A with $1\times10^7$ CFU of *Pseudomonas aeruginosa* in the acute lung injury model.
Figure 6:
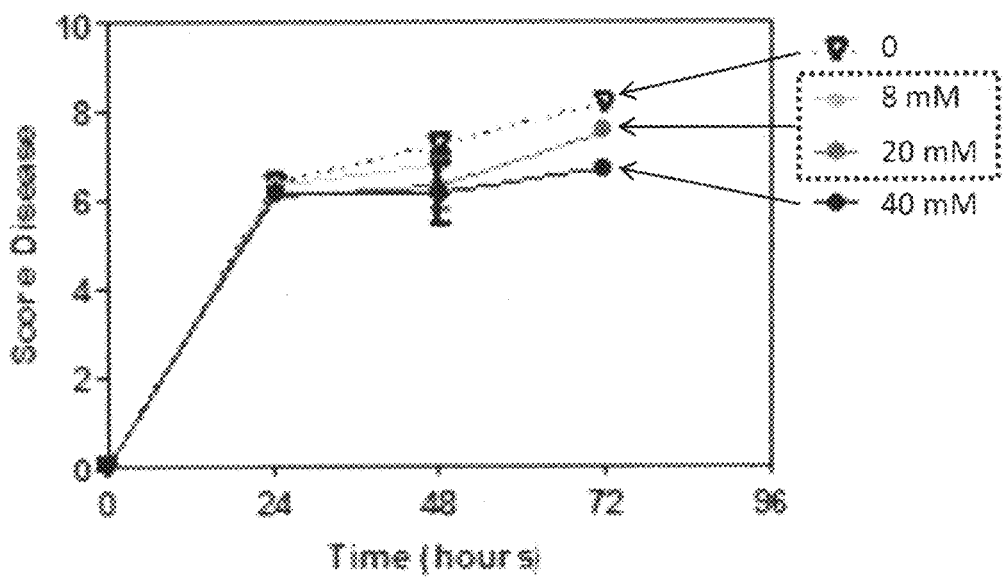

The animals were observed daily beginning 24 hours post infection and cumulative clinical (disease) scores were determined for each mouse (FIGS. 4 and 6). Parameters assessed were: (a) for appearance (smooth→bristly); (b) body temperature (normal→cold); (c) movement (moving→prostate); and (d) weight loss. Clinical scoring ranged from 0 (normal, uninfected appearance) to 10 (severely compromised).

Survival.

Animals were observed daily for morbidity/mortality and day of death recorded. Kaplan-Meier analysis was used to estimate survival function from life-span data and statistical values derived from a log rank test.

Results with Low Inoculum.

Figure 3:
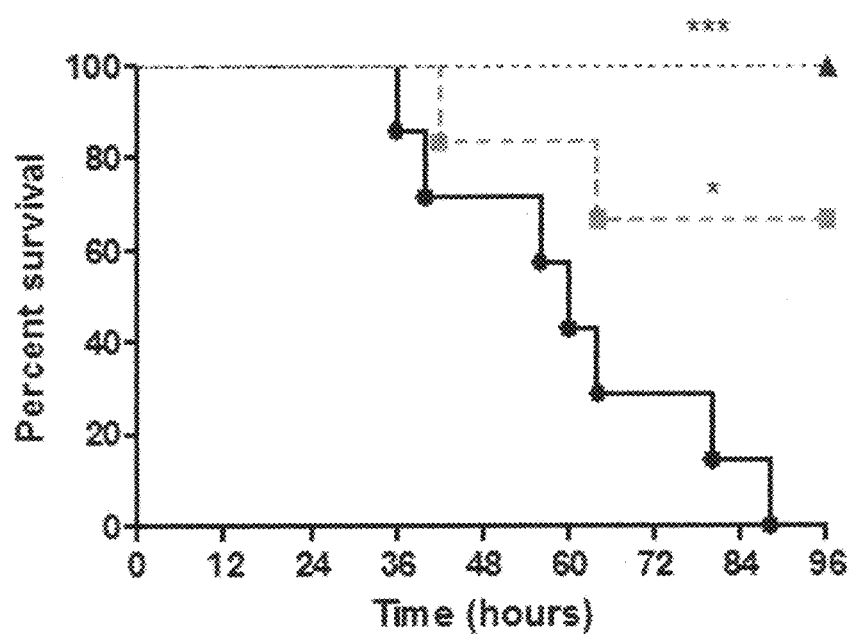
FIG. 3 depicts the percent survival following co-administration of saline, glycomimetic compound (I), or compound A with $2\times10^6$ CFU of *Pseudomonas aeruginosa* in the acute lung injury model.

Co-administration of $2\times10^6$ CFU of *Pseudomonas aeruginosa* with 40 mM glycomimetic compound (I) or compound A resulted in a survival benefit compared with animals co-administered saline (FIG. 3). Comparison of the glycomimetic compound (I) and compound A groups revealed that administration of glycomimetic compound (I) resulted in 100% survival (p<0.005 vs. saline) compared with 67% survival in the compound A treated group (p<0.05 vs. saline). There was no statistical difference noted between life-span of mice treated with glycomimetic compound (I) or compound A (p=0.13).

Results with High Inoculum.

Figure 5:
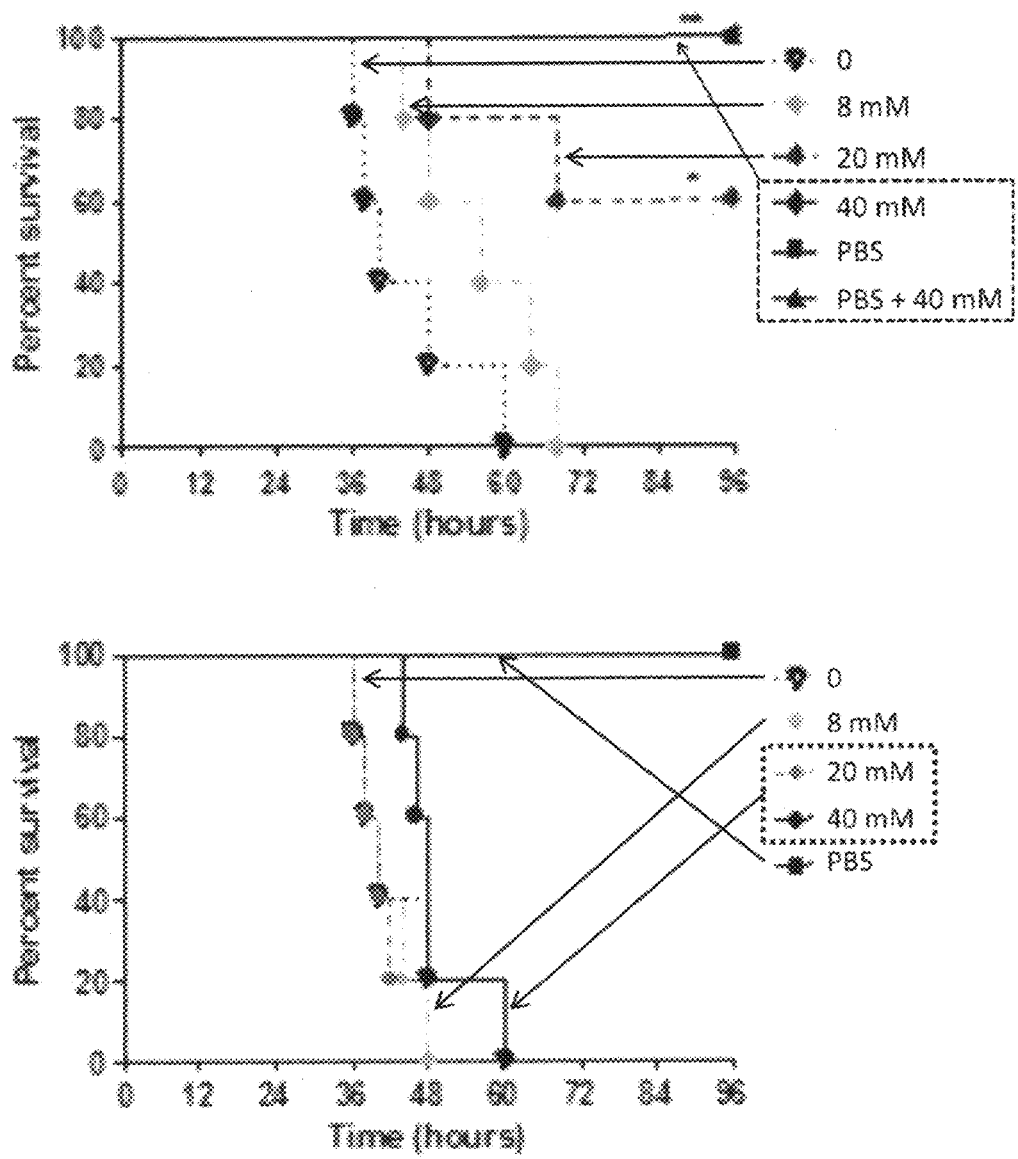
FIG. 5 depicts the percent survival following co-administration of saline, glycomimetic compound (I), or compound A with $1\times10^7$ CFU of *Pseudomonas aeruginosa* in the acute lung injury model.

In the more aggressive model of acute *Pseudomonas aeruginosa* lung infection co-administration of 20 or 40 mM glycomimetic compound (I) resulted in 60% (p<0.05 vs saline) and 100% (p<0.01 vs. saline) survival, respectively, at 96 hr (FIG. 5). Under identical experimental conditions, co-administration of compound A at equivalent doses did not impact survival. The improved efficacy of glycomimetic compound (I) in the high inoculum model was not the result of a non-specific toxic effect since no morbidity or mortality was observed in uninfected mice treated with 40 mM glycomimetic compound (I).

Example V

Acute Lung Injury Model—Treatment with Tobramycin

Figure 7:
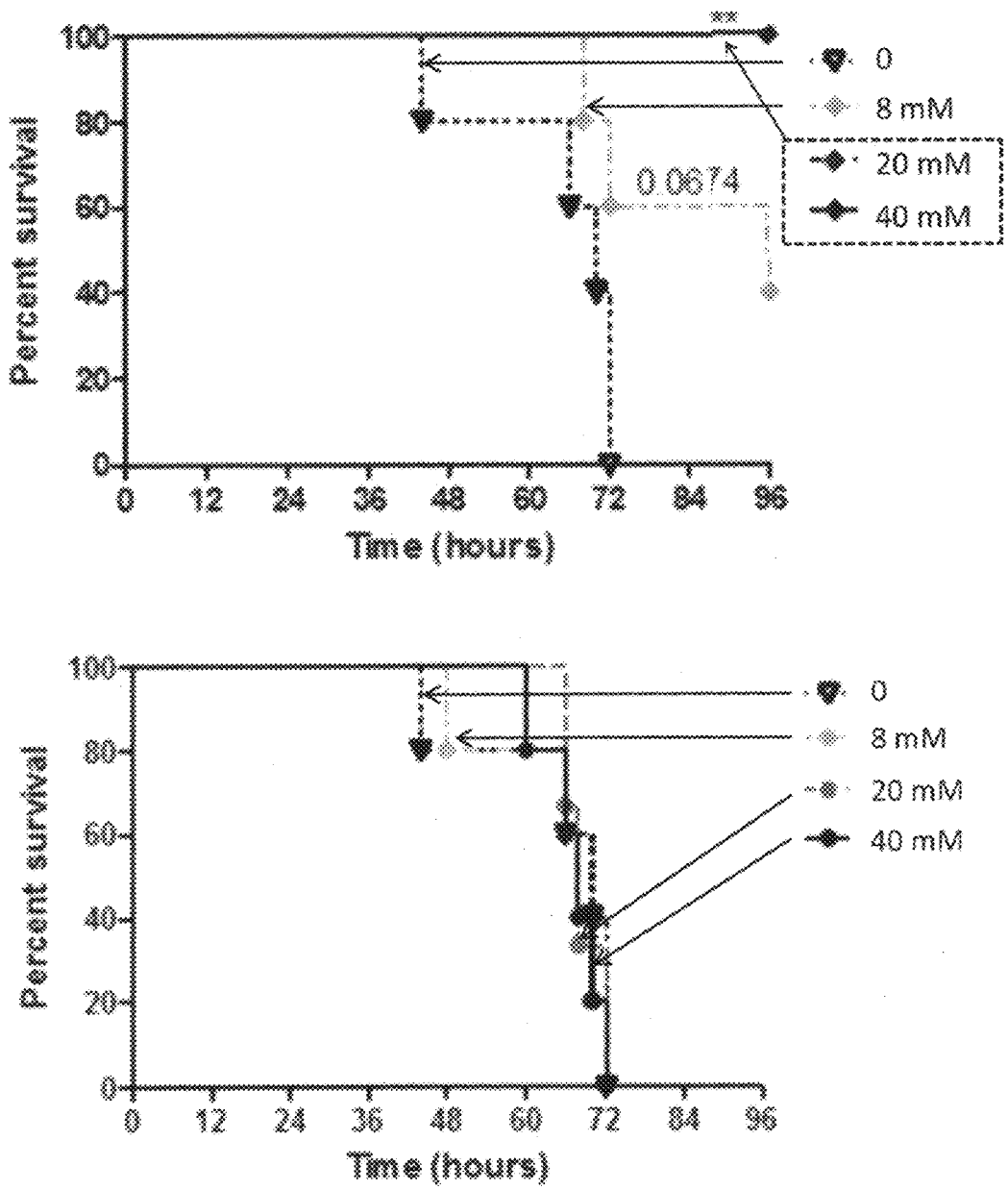
FIG. 7 depicts the percent survival following co-administration of saline, glycomimetic compound (I), or compound A with 1×10$^7$ CFU of *Pseudomonas aeruginosa* in combination with tobramycin in the acute lung injury model.

Mice were co-administered 2×107 CFU *Pseudomonas aeruginosa* with or without compound A or glycomimetic compound (I) in combination with 12 mg/kg tobramycin. The tobramycin was administered intraperitoneally 6 hours after bacterial challenge. Over the dose range studied (8, 20 and 40 mM), compound A administration together with tobramycin did not result in a survival benefit (FIG. 7). In contrast, survival was significantly increased following administration of tobramycin in combination with 8, 20 or 40 mM glycomimetic compound (I) (FIG. 7). The lowest dose group, 8 mM glycomimetic compound (I) resulted in 40% survival (p=0.0674 compared to saline), whereas the 20 and 40 mM dose levels resulted in to 100% survival in this model (p<0.01 vs. saline).

Example VI

Evaluation of Glycomimetic Compound (I)'s and Compound A's Effect as a Treatment in Acute Model of *P. aeruginosa*-Induced Infection in Mouse: Evaluation of the Compounds Activity in Association with Tobramycin at Different Inoculation Time Materials and Methods Bacterial Strains.

*Pseudomonas aeruginosa* PAO1 strain is a sequenced, well-characterized strain used as reference strain. Bacteria were grown overnight at 37° C. in Lysogeny Broth Lennox (LB) (BD Europe, Le pont de Claix, France) under orbital shaking (300 rpm) from frozen stock. A secondary culture was performed during 2 hours and before harvesting the bacteria by centrifugation (2000 g, 5 min), and two washings with sterile phosphate-buffered saline (PBS). Turbidity was then approximated by measurement of optical density at $A_{600}$ (Ultrospec 10 Cell Density Meter, General Electric, Fairfield, Conn.) and verified by serial dilution and plating on LB agar Plates.

Test and Control Articles.

Vehicle was phosphate buffered saline, and test solutions are Glycomimetic Compound (I) 40 mM in PBS, and Compound A 40 mM in PBS. Test articles were provided by GlycoMimetics and stored at −20° C. Tobramycin (1 g) was provided by Laboratoire EREMPHARMA (25 rue Greffulhe—92300 Levallois) and stored at (+4° C.).

Mouse Infection Pneumonia.

Male C57BL6/J mice (8 weeks old) purchased from Janvier Labs (Route du Genest, 53940 Le Genest-Saint-Isle) were housed a pathogen-free unit of the Lille University Animal Care Facility and allowed food and water ad lib.

Mice were anesthetized briefly with inhaled sevoflurane (Sevorane™, Abbott, Queensborough, UK), allowing maintenance of spontaneous breathing after which 50 µL of the bacterial solution were administered intranasally representing a total of $1.10^6$ CFU/mouse (except for tobramycin study conducted with lethal inoculate of $2.10^6$ CFU/mouse). Control mice receive 50 µL of PBS. All mice were sacrificed at 24 h (except for survival studies, mice were monitored on weight and clinical score 96 h post bacterial infection). Glycomimetic Compound (I) or Compound A were administered IN with the inoculum or post-infection (see FIG. 8 and FIG. 12). In appropriate groups, mice were treated 24 h after infection with 12 mg/kg tobramycin administered intraperitoneally.

Treatment Effect.

For each group, treatment effect was measured with the disease score and daily mortality rate post challenge. The evolution of the disease score assessing the clinical appearance of the animals was evaluated on 4 items scored from 0 to 10 summarized in Table 1 (body temperature, appearance of the bristle, behavior and weight loss; 0: healthy mice, 10 moribund mice). All disease score assessments were performed by two experimenters throughout the study.

TABLE 1

| Score disease parameters. | | | |
| --- | --- | --- | --- |
| | Movement | Fur | Temperature |
| 0 | Moving | Smooth | normal |
| 1 | Low mobility | Bristly | |
| 2 | prostrate | | cold |

(Clinical score = [(Fur score + temperature score + movement score) + (% weight loss/(−5))])

Statistical Analysis.

Statistical analysis was performed using Prism 5 software (Graph-Pad Software, San Diego Calif.). Values are expressed as mean±SEM. Comparison groups were analysed with the nonparametric Mann-Whitney test. Survival curves were analysed using Log-rank (Mantel-Cox) test. *p<0.05;  p<0.01; * p<0.001 Results are mean+/− Standard error.

Results: Monotherapy Experiments

Figure 8:
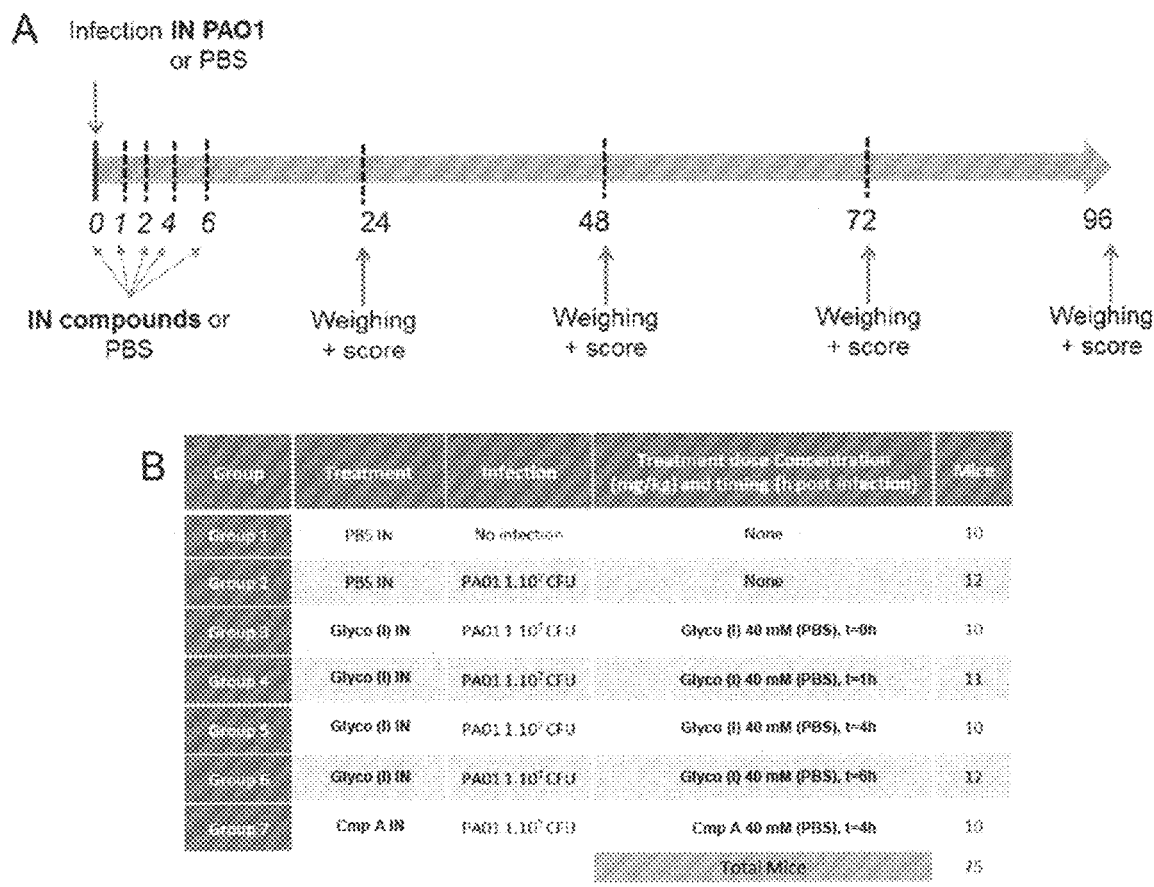
FIG. 8 depicts the treatment protocol (A) and groups distribution (B) following administration of 1×10$^7$ CFU of *Pseudomonas aeruginosa* in the acute lung injury model, evaluated at different inoculation times of either saline, glycomimetic compound (I), or compound A.

Mice, 8 weeks old C57Bl/6J male, received intranasally $1.10^7$ CFU of PaO1 and Glycomimetic Compound (I) or Compound A at different time points, as described in FIG. 8.

We analyzed weight loss, clinical disease score and mortality. Fourteen independent cohorts of 5 mice each were tested. Each cohort included an equal representation of testing conditions. All stage 1 cohorts were tested over 4 days. At the conclusion of Stage 1, there was a total of 10 mice for each of the above 7 treatment groups.

Figure 9:
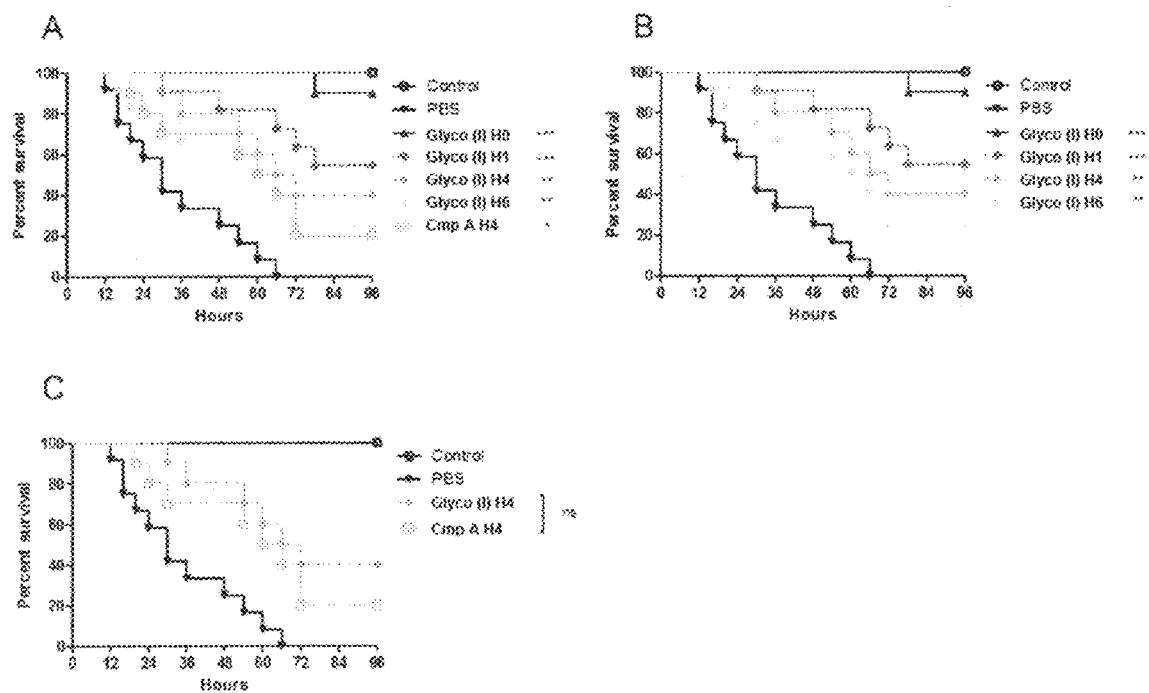
FIG. 9 depicts survival analysis, all the groups (A) different instillation time of glycomimetic compound (I) (B), comparison of the two compounds instillated at H4 p.i (C). Statistical analysis for each group against the control infected group.

All the mice infected without either Glycomimetic Compound (I) or Compound A treatment died at H66 compared to the not infected mice who survived during the experiment. Our results show a significant effect of Glycomimetic Compound (I) administrated with the bacteria on survival, a 90% survival is observed in this model after PAO1 administration (FIG. 9).

All the groups treated with the different compounds show a significant survival increase, the efficacy is better when the compound is injected early in the course of infection. An administration of Glycomimetic Compound (I) after one hour of infection leads to 54.5% survival, declining to 40% after 4 hours, and 25% after 6 hours. In comparison, Compound A after 4 hours of infection is associated to 20% survival. Survival is doubled at 4 hours for the mice treated with Glycomimetic Compound (I) compared to Compound A.

Figure 10:
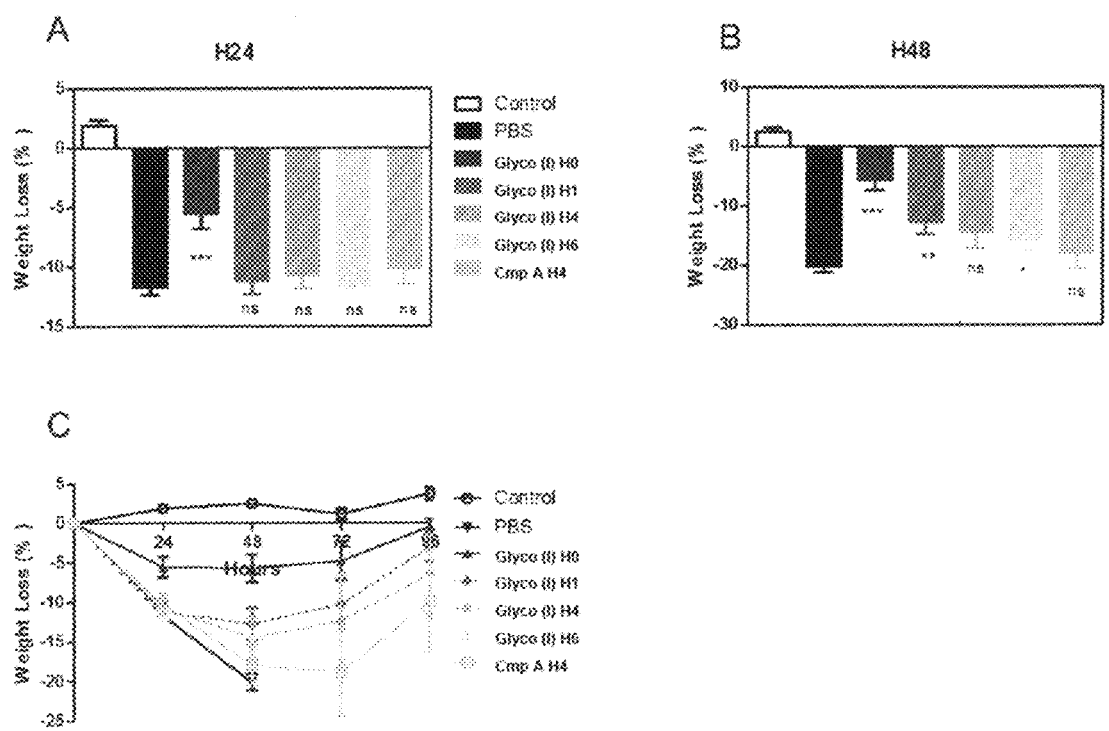
FIG. 10 depicts the weight loss analysis at H24 (A), H48 (B) and over time (C).
Figure 11:
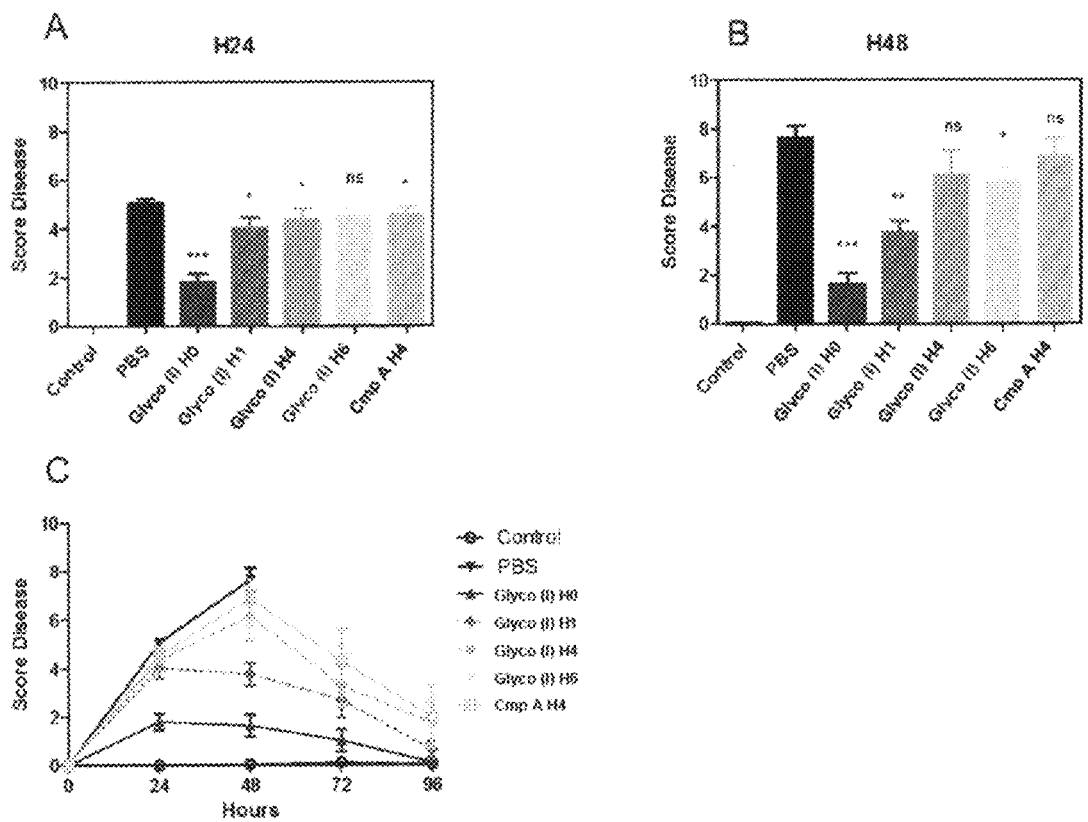
FIG. 11 depicts the score disease analysis at H24 (A), H48 (B) and over time (C).

The data observed both with weight loss and score disease are consistent with the survival studies. See FIGS. 10 and 11. We observe a positive effect on weight and score disease of the two compounds. Glycomimetic Compound (I) is superior to Compound A and efficacy is also associated to the timing of administration, the earlier the better.

Results: Association with Tobramycin

Figure 12:
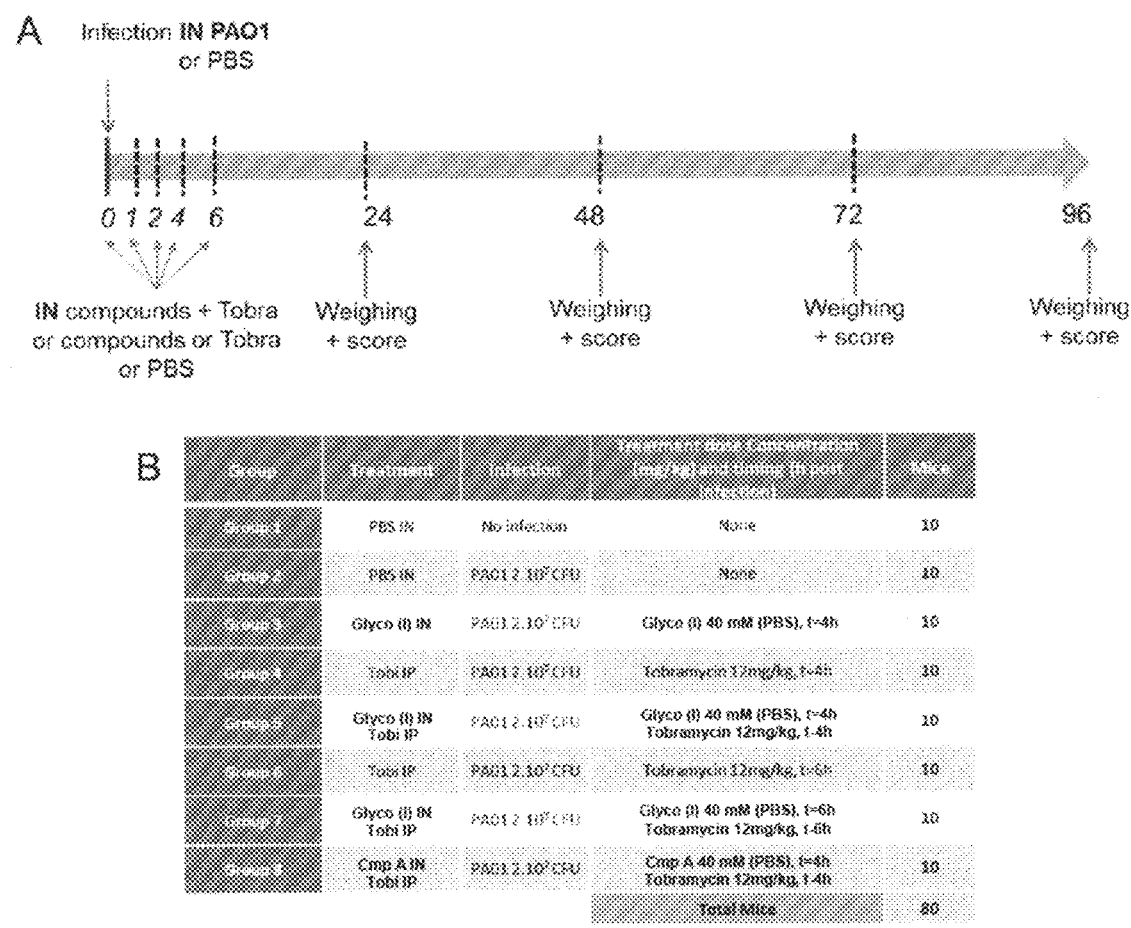
FIG. 12 depicts the treatment protocol (A) and groups distribution (B) following administration of 1×10$^7$ CFU of *Pseudomonas aeruginosa* in the acute lung injury model, evaluated at different inoculation times of either saline, glycomimetic compound (I), or compound A (alone or in combination with tobramycin).

Mice, 8 weeks old C57Bl/6J male, received intranasally 2.10$^7$ CFU of PAO1 and Glycomimetic Compound (I) or Compound A at different time points with or without an intraperitoneal injection of tobramycin 12 mg/kg (FIG. 12).

Figure 13:
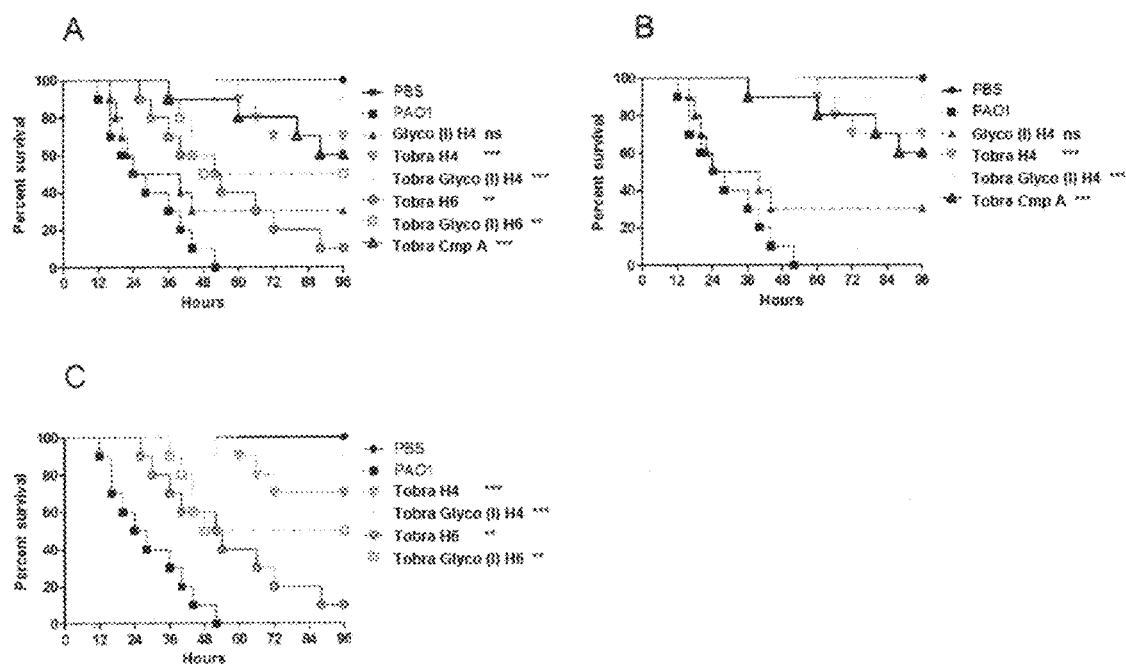
FIG. 13 depicts the survival analysis, all the groups (A), comparison of glycomimetic compound (I) and compound A instilled at H4 p.i (B), different instillation time of glycomimetic compound (I) (C). Statistical analysis were performed for each group with the control infected group.

The association of tobramycin shows very promising results with a synergism between Glycomimetic Compound (I) and tobramycin. See, e.g., FIG. 13. In fact, focusing on the H4 administration, Glycomimetic Compound (I) alone is associated to a 30% survival, tobramycin alone goes up to 70%, but the association reaches 90% survival. FIG. 13. Interestingly, at 6 h where tobramycin goes down to 10%, Glycomimetic Compound (I) to 20% (from FIG. 9) and the association reaches 50%. These data support the use of Glycomimetic Compound (I) as an adjuvant to the antibiotic providing a synergistic effect on survival.

Figure 14:
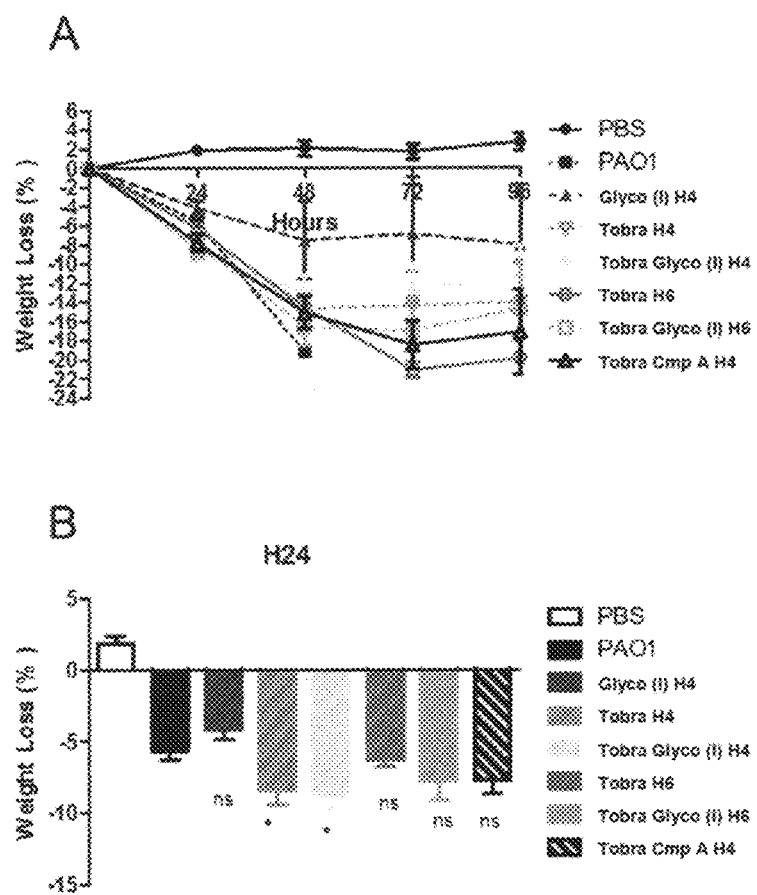
FIG. 14 depicts the weight loss analysis over time (A), at H24 (B).
Figure 15:
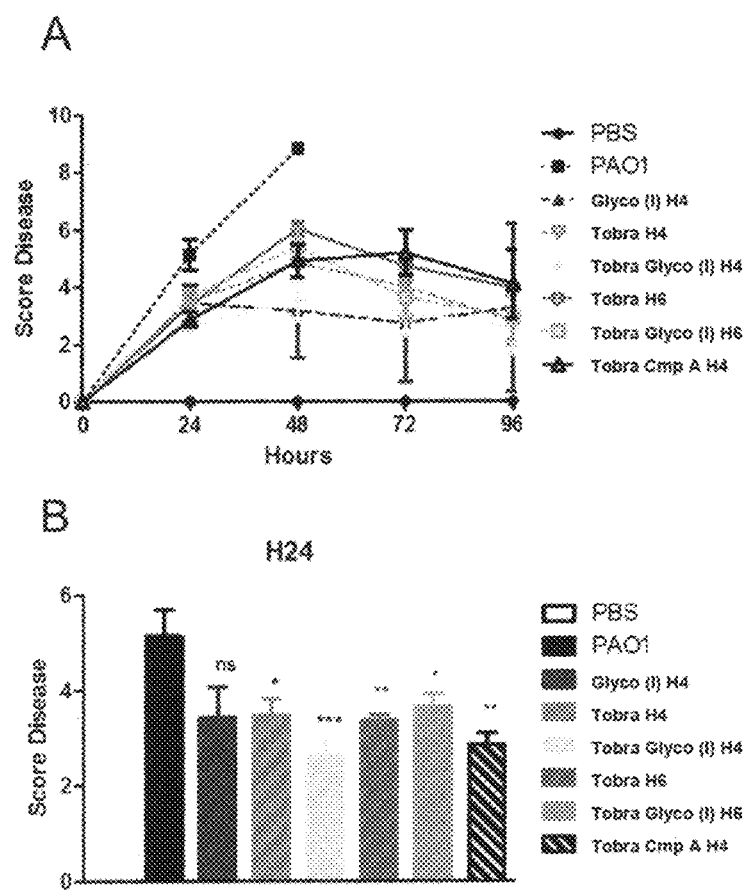
FIG. 15 depicts the score disease analysis over time (A), at H24 (B).

The analysis of the weight loss over time is interesting and provides some new insights on the infectious process (see FIG. 14). Weight loss is increased for the animal with the higher survival, it seems that the capacity to mobilize energy and increase the basic metabolism is associated to a better host response. The results observed with the score disease are also consistent with the survival data. FIG. 15. The two groups that received tobramycin and either Glycomimetic Compound (I) or Compound A are associated to a lower score at 4 hours.

DISCUSSION

We confirm, with the first set of experiments, a positive effect on survival of both Glycomimetic Compound (I) and Compound A. We show that the response is clearly time dependent, the earlier the compound is administered, the better is the survival. In this setting Glycomimetic Compound (I) is better than Compound A.

In the second set of experiments we observe a potential synergy between Glycomimetic Compound (I) and tobramycin with even the persistence of an effect when tobramycin alone at 6 hours does not change the survival prognosis. From the data obtained on the analysis of the weight loss, a putative mechanism could be an interaction with the host response with an increased metabolism.

Globally all these data suggest potential paths to explore specifically in the cystic fibrosis (CF) environment and particularly in the three classic phases of CF, as described below.

First Infection with *Pseudomonas*:

without being bound by theory, based on the mechanisms potentially involved to explain efficacy, one could argue that pre-emptive administration of Glycomimetic Compound (I) or Compound A may first reduce adhesion and colonization and second potentially influence the host response or even *Pseudomonas* basic metabolism towards virulence or colonization. A potential way to measure this aspect could be to use a chronic model and evaluate colonization potential as well as *Pseudomonas* metabolism (expression of Las/Rhl/alginate over time). Seven days model in mice may provide these answers.

Establishment of *Pseudomonas* Over Time:

the model we developed cannot go beyond 7 days, to see if Glycomimetic Compound (I) or Compound A (or these compounds in combination with antibiotic) can modify *Pseudomonas* colonization over time, a model lasting at least 3 weeks may be required. From the previous data (specifically the association data), a role can be hypothesized.

Exacerbation:

The results support that Glycomimetic Compound (I) and Compound A alone is efficient and the association with tobramycin is also very efficient, and suggest possible clinical significance for inhaled Glycomimetic Compound (I) and Compound A. Knowing that tobramycin is used in aerosol in CF, a clinical evaluation of the combination is supported.

What is claimed is:

1. A method for the treatment and/or prevention of at least one disease, disorder, and/or condition where inhibition of PA-IL and/or PA-IIL is useful, the method comprising administering to a subject in need thereof an effective amount of at least one compound chosen from:

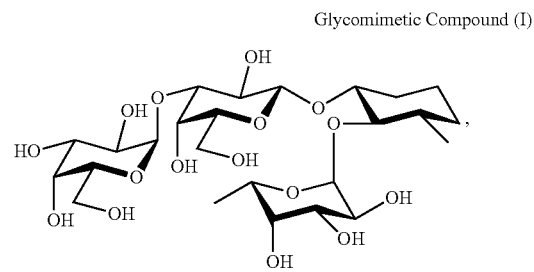

Glycomimetic Compound (I)

prodrugs thereof, and pharmaceutically acceptable salts of any of the foregoing, wherein the at least one disease, disorder, and/or condition involves infections with and/or colonization by *Pseudomonas* bacteria.

2. The method according to claim 1, wherein the *Pseudomonas* bacteria are *Pseudomonas aeruginosa*.

3. The method according to claim 2, wherein the *Pseudomonas* bacteria are in the lungs of the subject.

4. The method according to claim 3, wherein the at least one disease, disorder, and/or condition is chosen from cystic fibrosis, ventilator-associated pneumonia, bronchiectasis, and chronic obstructive pulmonary disease.

5. The method according to claim 3, wherein the at least one disease, disorder, and/or condition is cystic fibrosis.

6. A method for inhibiting an infection with and/or colonization by *Pseudomonas* bacteria, the method comprising administering to a subject in need thereof an effective amount of at least one compound chosen from:

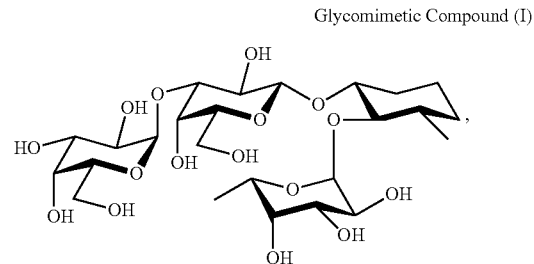

Glycomimetic Compound (I)

prodrugs thereof, and pharmaceutically acceptable salts of any of the foregoing.

7. The method according to claim 6, wherein the *Pseudomonas* bacteria are *Pseudomonas aeruginosa*.

8. The method according to claim 7, wherein the infection and/or colonization by *Pseudomonas* bacteria are in the lungs of the subject.

9. A method for the treatment of cystic fibrosis, the method comprising administering to a subject in need thereof an effective amount of at least one compound chosen from:

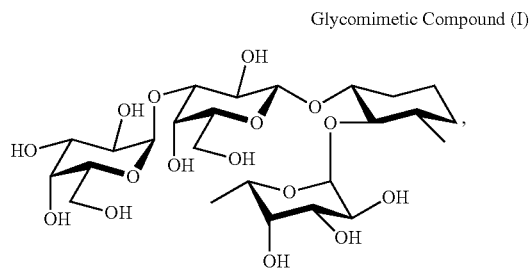

Glycomimetic Compound (I)

prodrugs thereof, and pharmaceutically acceptable salts of any of the foregoing.

10. The method according to any one of claim 1, 6, or 9, wherein the at least one compound is administered in combination with a second therapeutic agent.

11. The method according to claim 10, wherein the second therapeutic agent is an anti-bacterial agent.

12. The method according to claim 11, wherein the anti-bacterial agent is tobramycin.

13. The method according to any one of claim 1, 6, or 9, wherein the at least one compound is conjugated to a therapeutic or diagnostic agent.

14. The method according to claim 13, wherein the at least one compound is conjugated to a therapeutic agent.

15. The method according to claim 14, wherein the therapeutic agent is an anti-bacterial agent.

16. The method according to claim 15, wherein the anti-bacterial agent is tobramycin.

17. The method according to any one of claim 1, 6, or 9, wherein the at least one compound is administered in combination with at least one pharmaceutically acceptable carrier or diluent.

18. The method according to any one of claim 1, 6, or 9, wherein the at least one compound is

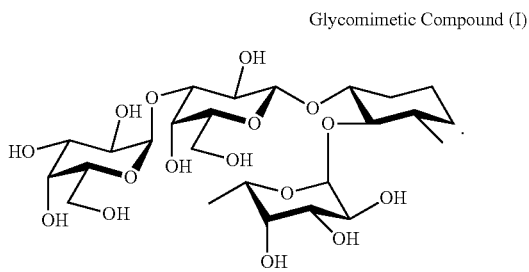

Glycomimetic Compound (I)

\* \* \* \* \*